United States Patent [19]
Loh

[11] 4,429,119
[45] Jan. 31, 1984

[54] 5-DEOXY-3-O-ARYLMETHYL OR SUBSTITUTED ARYLMETHYL-1,2-O-ALKYLIDENE-ALPHA-D-XYLOFURANOSE HERBICIDE DERIVATIVES

[75] Inventor: William Loh, Petaluma, Calif.

[73] Assignee: Chevron Research Company, San Francisco, Calif.

[21] Appl. No.: 409,236

[22] Filed: Aug. 18, 1982

[51] Int. Cl.$^3$ .................. C07H 17/04; A01N 43/08
[52] U.S. Cl. ................................. 536/181; 536/184; 536/4.1; 71/88
[58] Field of Search .................. 536/4.1, 18.1

[56] References Cited

U.S. PATENT DOCUMENTS

| | | | |
|---|---|---|---|
| 3,699,103 | 10/1972 | Kiss | 536/18.1 |
| 3,919,252 | 11/1975 | Barker et al. | 260/340.9 |
| 4,116,669 | 9/1978 | Barkeer et al. | |
| 4,146,384 | 3/1979 | Schmidt et al. | |
| 4,207,088 | 6/1980 | Kornz | |

FOREIGN PATENT DOCUMENTS 55-154992 12/1980 Japan .................................. 536/4.1

OTHER PUBLICATIONS

Carbohyd. Res. 7, 161 (1968).
J. Amer. Chem. Soc. 78, 2846 (1956).
Methods in Carbohyd. Chem. vol. VI 297 (1972).
Tetrahedron Letters No. 26, pp. 2447-2448 (1979).
Tetrahedron Letters No. 35, pp. 3233-3236 (1978).
J. Chem. Soc. Jap., Chem. Ind. Chem. 1981(5), 769-775 Chem. Absts.
Synthesis 636 (1980).
J. Chem. Soc. Perkin Trans I. 38 (1973).
J. of Organic Chemistry 46, (1981), pp. 1296-1309.
J. of Organic Chemistry 44, (1979), pp. 4294-4299.
Carbohydrate Research 29, (1973), pp. 311-323.
J. Org. Chem., 27, 2107 (1962).
Chem. Ber 102, 820 (1969).
Helv. Chim. Acta 56, 1802 (1973).
Carbohydrate Research 31 (1973), pp. 387-396.
Bulletin of the Chem. Society of Japan, 51 (12) (1978).

*Primary Examiner*—Johnnie R. Brown
*Attorney, Agent, or Firm*—D. A. Newell; T. G. De Jonghe; L. S. Squires

[57] ABSTRACT

5-Deoxy-3-O-arylmethyl or substituted arylmethyl-1,2-O-alkylidene-a-D-xylofuranose and 5-C-alkyl and alkenyl derivatives thereof. The compounds are useful as herbicides and plant growth regulators.

15 Claims, No Drawings

5-DEOXY-3-O-ARYLMETHYL OR SUBSTITUTED ARYLMETHYL-1, 2-0-ALKYLIDENE-ALPHA-D-XYLOFURANOSE HERBICIDE DERIVATIVES

BACKGROUND OF THE INVENTION

This invention relates to 5-deoxy, 5-C-alkyl and 5-C-alkylidene-5-deoxy-3-O-arylmethyl and substituted arylmethyl-1,2-O-alkylidene-a-D-xylofuranoses and to application of 5-deoxy-3-O-arylmethyl, and substituted arylmethyl-1,2-O-alkylidene-a-D-xylofuranoses and 5-C-alkyl and 5-C-alkenyl derivatives thereof as herbicides and plant growth regulators. The invention also relates to the preparation of such compounds.

The laboratory preparation of 3-O-benzyl-5-deoxy-1,2-O-isopropylidene-a-D-xylofuranose for the purpose of conducting academic sugar studies is referenced in Tetrahedron Letters No. 26, pp. 2447–2448 (1979). The preparation of 3-O-benzyl-5-deoxy-1,2-O-isopropylidene-5-C-propyl-a-D-xylofuranose as an intermediate in the multistep synthesis of the antibiotic (-)-Canadensolide is described in Tetrahedron Letters No. 35, pp. 3233–3236 (1978) and J. Chem. Soc. Jap., Chem. Ind. Chem. 1981(5), 769–755 Chem. Abstracts, Vol. 83, issue 932, (1981), Abstract No. 317647. The laboratory preparation of 3-O-benzyl-5-deoxy-5-C-methylene-1,2-O-isopropylidene-a-D-xylofuranose relative to certain academic studies is described in numerous publications, including Synthesis 636 (1980); Tetrahedron Letters 4841 (1979); Carbohydrate Research 48, 143 (1976) Tetrahedron Letters 2623 (1975); Helv. Chim Acta 1303 (1973); J. Chem. Soc. Perkin Trans I. 38 (1973); Carbohyd. Research 26, 230 (1973); Carbohyd. Research 22, 227 (1972); Carbohyd. Research, 215 (1970); J. Amer. Chem. Soc. 78, 2846 (1956); Carbohyd. Res. 7, 161 (1968), Methods in Carbohyd. Chem. Vol. VI 297 (1972).

The laboratory preparation of 3-O-benzyl-5-deoxy-5-C-ethylmethylene-1,2-O-isopropylidene-a-D-xylofuranose is described in Tetrahedron Letters 3233 (1978) and the laboratory preparation of 3-O-benzyl-5,6-dideoxy-1,2-O-isopropylidene-5-C-methylene-a-D-xylo-hexofuranose is described in Helvetica Chimica Acta 58, 1501 (1975).

The laboratory preparation of 3-O-benzyl-6,7-dideoxy-1,2-O-isopropylidene-a-D-xylo-heptofuranos-5-ulose and/or 3-O-benzyl-6-deoxy-1,2-O-isopropylidene-a-D-xylohexofuranos-5-ulose for academic studies is described in Carbohydrate Research 31 (1973), pages 387–396; Carbohydrate Research 29 (1973), pages 311–323; Bulletin of the Chemical Society of Japan, 51 (12) (1978), pages 3595–3598; Journal of Organic Chemistry 44 (1979), pages 4294–4299 and Journal of Organic Chemistry 46, (1981), pages 1296–1309. Helv. Chim. Acta 56, 1802 (1973); Carbohydrate Research 26, 441 (1973); Chem. Ber. 102, 820 (1969) and J. Org. Chem. 27, 2107 (1962).

U.S. Pat. Nos. 4,116,669, 4,146,384 and 4,330,320 and German Pat. DS No. 2,860,975 disclose a broad range of tetrahydrofuran derivatives and attribute herbicidal activity to these derivatives. U.S. Pat. Nos. 3,919,252, 4,004,911 and 4,207,088 disclose dioxalane derivatives and dioxane derivatives and attribute grass herbicidal activity to these derivatives. The sodium salt of 2,3:4,6-bis-O-(1-methylethylidene)-O-(L-xylo-2-hexulofuranosonic acid) is sold as a pinching agent for azaleas and ornamentals and a growth retardant for shrubs, hedges and ground covers and is disclosed in U.S. Pat. No. 4,007,206.

The application of 5-C-alkyl-3-O-benzyl-1,2-O-isopropylidene a-D-xylo-pentodialdofuranose as herbicides and plant growth regulators is described by B. McCaskey in commonly assigned copending application Ser. No. 387,590 filed June 11, 1982.

SUMMARY OF THE INVENTION

The present invention provides compounds having herbicidal activity and plant growth regulating activity and provides method and compositions for preventing or retarding unwanted vegetation and for controlling the growth of vegetation. Certain of the active compounds are composed only of hydrogen, oxygen and carbon and hence are very desirable from an environmental standpoint because they decompose into innocuous carbon-oxygen moieties and water. I have further found that biological activity in tetrahydrofuranyl nucleolus compounds is very unpredictable. For example, even though the compounds and compositions of the present invention exhibit very good herbicide activity, especially grass pre-emergence herbicide activity, and plant growth regulating activity, a number of closely related analogs and even the 3-epimers of the present compounds fail to exhibit such activity.

In one aspect the invention provides compounds having the formula

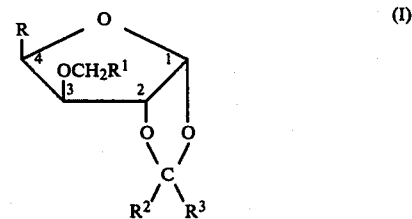

wherein
R is alkyl having 1 through 4 carbon atoms or alkenyl having 2 through 4 carbon atoms;
$R^1$ is 2-trifluoromethylphenyl, aryl having 6 through 10 carbon atoms, or substituted aryl having 1 through 4 substituents independently selected from the group of lower alkyl, lower alkoxy, and halo, with the proviso that when $R^1$ is substituted aryl having more than two halo substituents or is 2,3- or 3,4-dihalophenyl, then R is alkyl; and
$R^2$ or $R^3$ is hydrogen or lower alkyl with the proviso that when R is methyl, butyl, vinyl, 2-allyl, or but-1-enyl, $R^2$ is methyl and $R^3$ is methyl, then $R^1$ is not phenyl.

The present invention provides a herbicidal composition comprising a carrier and a herbicidally effective amount of a compound having the formula:

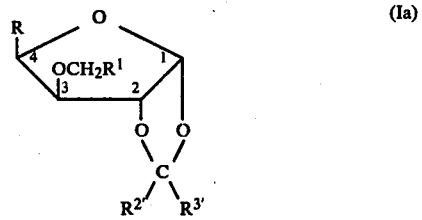

wherein
R is alkyl having 1 through 4 carbon atoms or alkenyl having 2 through 4 carbon atoms;
R¹ is 2-trifluoromethylphenyl or aryl having 6 through 10 carbon atoms, or substituted aryl having 1 through 4 substituents independently selected from the group of lower alkyl, lower alkoxy, halo, with the proviso than when R¹ is 2,4- or 3,4-dihalophenyl or has more than two halo substituents, then R is said alkyl; and
R²' or R³' is hydrogen or lower alkyl.

The compounds of Formulas I and Ia are (D) optically active and can comprise various isomers. Formulas (I) and (Ia) are intended to represent the respective pure isomers as well as mixtures thereof, having the relative orientations at the 1–2, 3 and 4 positions shown in Formulas (I) and (Ia), and such respective isomers and mixtures are encompassed within the invention.

The present invention also provides a method for preventing or controlling the growth of unwanted vegetation, especially grasses, which comprises treating the growth medium and/or the foliage of such vegetation with a herbicidally effective amount of the compound of Formula Ia.

In another aspect, the present invention provides a plant growth regulating composition comprising a carrier and an effective amount of the plant growth regulating compound of the Formula Ia.

The present invention also provides a method for regulating plant growth which comprises treating the growth medium and/or the foliage of such vegetation with a plant growth regulating effective amount of the compound of Formula Ia.

The present invention also provides chemical intermediates and processes for preparing the compounds of Formula Ia, for example, the compounds of Formula Ia, wherein R is alkenyl, are useful as intermediates for the compounds of Formula Ia, wherein R is alkyl.

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 4, 7 and 10–16 set forth hereinbelow on pages 25, 35 and 40–45. In terms of substituents the preferred compounds are those wherein R is alkyl, especially ethyl or propyl. The preferred R¹ substituent is aryl and monosubstituted aryl having a single substituent selected from the group lower alkyl, lower alkoxy, and halo. More preferably, R¹ is phenyl or 2-substituted phenyl especially phenyl, 2-methylphenyl or 2-halophenyl, especially 2-fluorophenyl and 2-chlorophenyl. Preferably, R² and R³ are independently hydrogen, methyl or ethyl and especially wherein R² and R³ are each methyl.

The compounds of Formula Ia can be prepared via the process schematically represented by the following overall reaction equation.

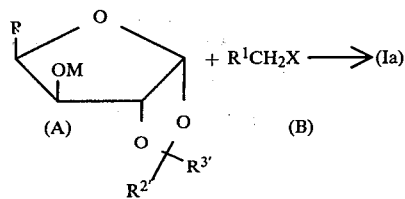

wherein R, R¹, R² and R³ are as defined hereinabove, X is chloro or bromo and M is an alkali metal cation preferably sodium.

This process can be effected by contacting compound (A) with compound B, having the appropriate R¹ group, preferably in an inert organic solvent (e.g., tetrahydrofuran) and in the presence of an appropriate catalyst. This process is typically conducted at temperatures in the range of about from 0° to 140° C., preferably about from 25 to 75, for about from 1 to 48 hours, preferably about from 3 to 12 hours. Typically about from 1.0 to 1.25 moles, and preferably about from 1.0 to 1.1 moles of (B) are used per mole of compound A.

Suitable inert organic solvents which can be used include, for example, tetrahydrofuran, ethyl ether, xylene, toluene, dimethylsulfoxide, dimethylformamide, and the like and compatible mixtures thereof. Suitable catalysts which can be used include, for example, tetrabutylammonium iodide, tetrabutylammonium bromide, benzyltriethylammonium chloride, and the like. Typically a catalyst to reactant (A) ratio of about from 0.01 to 0.1 mole of catalyst per mole of A is used. Generally, best results are obtained using tetrahydrofuran as the solvent, tetrabutylammonium iodide as the catalyst and conducting the reaction at about from 25° to 65° C. for about from 3 to 12 hours. Compound Ia can be separated from the reaction product mixture via any suitable procedure; for example, chromatographically. For example, the separation of the compound of Formula Ia, wherein R is methyl, R¹ is phenyl and R² and R³ are each methyl, is described in Tetrahedron Letters No. 26, pp. 2447–2448 (1979).

Also, because of interfering reactions the compounds of Formula (Ia) wherein one or both of R²' or R³' are hydrogen are best prepared from the corresponding R² and R³ are each alkyl compounds of (Ia), as will be subsequently described.

Compound A can be conveniently prepared by reacting the corresponding 3-position hydroxy compound (i.e., M is hydrogen) with an alkali metal base such as sodium hydride, potassium hydride, sodium hydroxide; potassium hydroxide and the like. Typically, this reaction is conducted at about from 0° to 140° C. preferably about from 0° to 65° C., for about from 0.5 to 12 hours, preferably 0.5 to 1 hour, using about from 1.0 to 1.1 moles of alkali metal base per mole of the hydroxy analog of compound A. Conveniently, the same inert organic solvents as described above are also used thus facilitating in situ preparation of compound IA as described above. The appropriate 3-hydroxy analogs wherein R is alkyl having 2 through 4 carbon atoms can be prepared via the following schematically represented process:

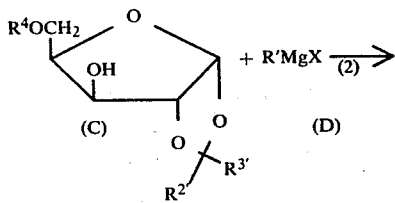

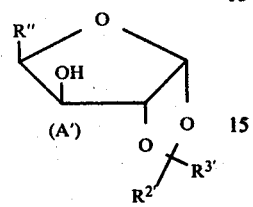

wherein R' is alkyl having 1 through 3 carbon atoms; R" is alkyl having 2 through 4 carbon atoms; $R^4O$ is an easily replaced group; X is chloro, bromo, or iodo and $R^{2'}$ and $R^{3'}$ are as defined hereinabove.

The first step of this process can be effected by contacting compound (C) with a Grignard reagent (D) having the appropriate R' group, preferably in an inert organic solvent (e.g., ethyl ether) and in the presence of a suitable catalyst. This step is typically conducted at temperatures in the range of about from −78° to 65° C. preferably about from 25° to 65° C. for about from 1 to 24 hours. Conveniently the reaction is conducted using about from 2 to 20 preferably about from 5 to 8 moles of compound D per mole of compound C.

Suitable inert organic solvents which can be used include, for example, ethyl ether and tetrahydrofuran and the like and compatible mixtures thereof. Suitable catalysts which can be used include, for example, dilithium tetrachlorocuprate ($Li_2CuCl_4$); ferric chloride, and the like and compatible mixtures thereof. Typically, a catalyst ratio of about from 0.001 to 0.01 mole of catalyst is used per mole of compound C.

As indicated above $R^4O$ is a group which is easily replaced by the R' moiety of the Grignard reagent. $R^4$ can, for example, be the group having the formula

wherein $R^5$ is phenyl, p-methylphenyl, lower alkyl. Very good results are typically obtained when $R^4$ is tosyl or mesyl. The compounds of Formula C are generally known compounds and can be prepared by known procedures or by obvious modifications thereof. For example, the compounds of Formula C wherein $R^4$ is tosyl or hydrogen and $R^2$ and $R^3$ are each methyl are described in Methods in Carbohydrate Chem. Vol. II 249 (1963). Analogs having different $R^4$ leaving groups can be obtained by reacting the 3-position hydroxy compound with a halide derivative of the leaving group. The 1,2-O-isopropylidene substituent in the starting material can be prepared by reacting the corresponding known 1,2,3,5-tetrahydroxy analog with dimethyl ketone to yield the corresponding 1,2:3,5-di-O-isopropylidene analog, see J. Amer. Chem. Soc. 77, 5900 (1955). The 3,5-O-alkylidene group can be selectively cleaved without cleaving the 1,2-O-alkylidene group by mild acid hydrolysis, see also J. Amer. Chem. Soc., 77, 5900 (1955). 1,2-O-isopropylidene-a-D-xylofuranose is also available commercially. Variation in the $R^2$ and $R^3$ substituents can be obtained by replacing dimethyl ketone with the appropriate ketone or aldehyde, for example, diethyl ketone, acetaldehyde, formaldehyde, methyl ethyl ketone, etc.

The compounds of Formula A' wherein R is methyl can be obtained by the process schematically represented by the following overall reaction sequence:

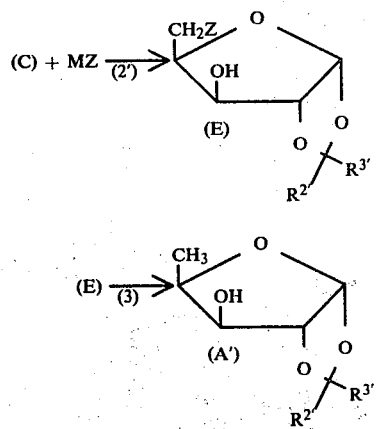

wherein M, $R^{2'}$ and $R^{3'}$ are as defined hereinabove, and Z is iodo or bromo.

Step 2' can be effected by contacting compound C with an alkali metal bromide or iodide (for example, sodium iodide) preferably a suitable inert organic solvent. This process is typically conducted at temperatures in the range of about from 50° to 100° C., preferably about from 80° to 90° C. for about from 5 to 48 hours. Typically about from 1.0 to 5.0, preferably about from 1.5 to 2.0 moles of alkali halide are used per mole of compound (C). Suitable inert organic solvents which can be used include for example 2-butanone, 2-pentanone, 3-pentanone, and the like. Conveniently, the reaction is conducted at the reflux temperature of the solvent. The synthesis of 5-deoxy-5-iodo-1,2-O-isopropylidene-a-D-xylofuranose where Z is iodo and $R^2$ and $R^3$ are each methyl is also described in J. Med. Chem. 22, 28 (1979).

Step 3 is conducted by contacting compound E with hydrogen in the presence of a suitable hydrogenation catalyst preferably in an inert organic solvent and preferably in the presence of a suitable scavenger base. This reaction is typically conducted at temperatures in the range of about from 0° to 50° C., conveniently 15° to 30° C., for about from 1 to 5 hours. Typically about from 1 to 10 moles of hydrogen ($H_2$) is used per mole of compound E. Suitable inert organic solvents which can be used include, for example, lower alkanols (e.g. methanol), and ethanol, ethyl acetate, and the like and compatible mixtures thereof.

Since this process yields hydrogen iodide or hydrogen bromide as a byproduct, it is preferred to conduct the reaction in the presence of a scavenger base to react with the hydrogen halide byproduct. Suitable scavenger bases which can be used include, for example, triethylamine, pyridine, and the like and compatible mixtures thereof.

Step 3 can also be conducted by employing $LiAlH_4$ as the reducing agent. The synthesis of 5-deoxy-1,2-O-isopropylidene-a-D-xylofuranose is also described in J. Chem. Soc. 2140 (1953).

The compounds of Formula Ia wherein R is isopropyl can be prepared by the following schematically represented process:

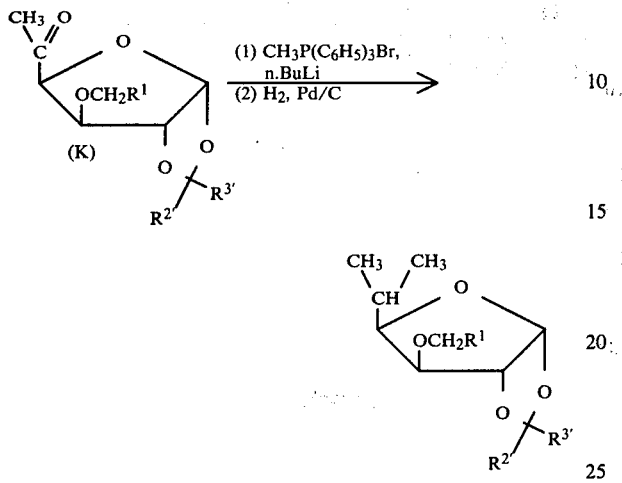

The first step of this process can be effected by contacting the compound of Formula K with triphenylmethyl phosphonium bromide and n-butyllithium preferably in an inert organic solvent. Typically, this step is conducted at temperatures in the range of about from 0° to 70° C., preferably about from 20° to 30° C., using about from 0.8 to 3 moles of triphenylmethyl phosphonium bromide and about from 0.5 to 3 moles of butyllithium per mole of compound K. Suitable solvents which can be used, include for example, tetrahydrofuran, benzene, hexane, dimethylsulfoxide, dimethoxyethane and the like. The alkene product of this reaction can be separated or desired as the product or hydrogenated to the alkyl. The second step is thus conducted by contacting the alkene reaction product with hydrogen in the presence of a suitable hydrogenation catalyst (for example palladium on carbon) in an inert organic solvent. Typically, the hydrogenation is conducted at temperatures in the range of about from 15° to 50° C. using about from 0.9 to 3 moles of hydrogen per mole of intermediate. Typically, the reaction is conducted by simply contacting the alkene product with hydrogen until no further hydrogen is taken up. The same inert organic solvents as used for the first step can also be used for the hydrogenation and the hydrogenation can be conveniently conducted in situ.

The compounds of Formula Ia wherein R is vinyl can be prepared by the process schematically represented by the following overall reaction equation sequence:

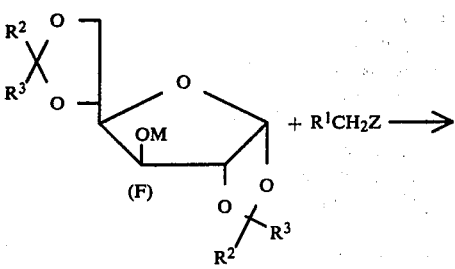

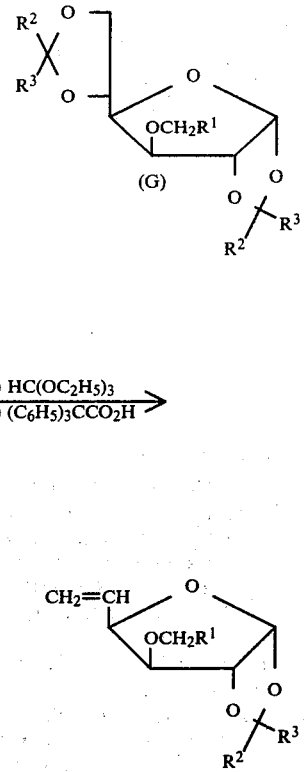

wherein $R^1$, $R^2$, $R^3$, M, and Z are as defined hereinabove.

The first step of this process can be effected in the same manner as described hereinabove, with respect to the reaction of compound A to compound Ia.

The starting material of Formula F can be prepared from the known 1,2,3,5,6-pentahydroxy substrate by reaction with the appropriate ketone as already described above.

In the next step the 5,6-O-alkylidenyl group is selectively cleaved. This can be conveniently effected by mild acid hydrolysis, for example, by contacting compound G with aqueous acetic acid at temperatures in the range of about from 25° to 100° C.; preferably about from 40° to 60° C. for about from 1 to 48 hours. Conveniently, the hydrolysis is conducted in a suitable inert organic solvent, such as for example aqueous acetic acid, aqueous trifluoroacetic acid, aqueous hydrochloric acid, and the like, and compatible mixtures thereof. The preparation of the compounds of Formulas F, G, and H, wherein $R^1$ is phenyl and $R^2$ and $R^3$ are each methyl, is also described in methods in Carbohydrate Chem. Vol. VI 286 and 297 (1972).

The last step, conversion of the 5,6-dihydroxy group to the olefin, is conveniently conducted in two phases. The first phase can be conducted by contacting compound H with a trialkylorthoformate (e.g. triethylorthoformate) under protic conditions to yield the corresponding 5,6-O-alkoxyalkylene derivative of compound H.

This phase is conveniently conducted at temperatures in the range of about from 100 to the boiling point of the trialkylorthoformate, preferably 120° to 146° C. for about from 3 to 12 hours. Preferably, small amount of a weak acid (e.g. acetic acid) is added to the reaction mixture to ensure protic conditions.

The next phase of this step can be effected by heating the product of the first phase in the presence of an acid. This phase is typically conducted at temperatures in the range of about from 160° to 180° C. for about from 3 to 6 hours. Suitable acids which can be used include, for example, triphenylacetic acid, benzoic acid, p-chlorobenzoic acid, and the like. The example wherein $R^1$ is phenyl, and $R^2$ and $R^3$ are each methyl, is described in Methods in Carbohydrate Chem. Vol. VI 297 (1972).

The compounds of Formula Ia wherein R is alkenyl having 3 or 4 carbon atoms having its double bond at the 1' position can be made by the following procedure:

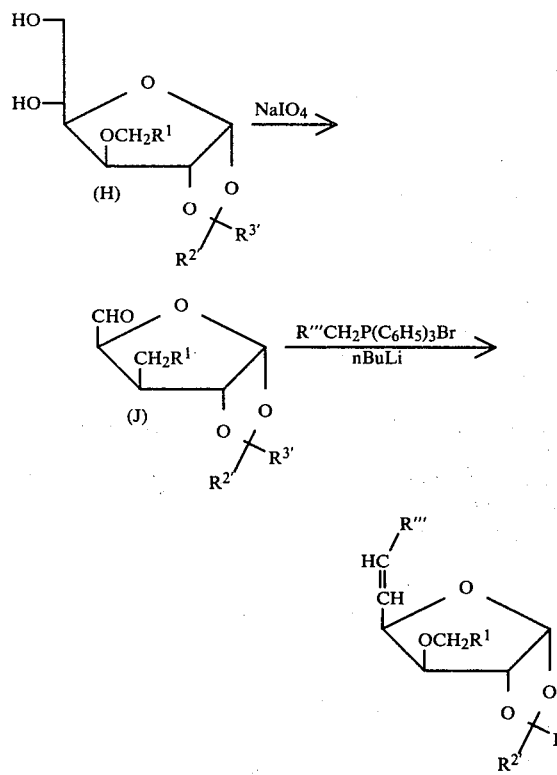

wherein $R'''$ is alkyl having 1 to 2 carbon atoms; and $R^1$, $R^2$, and $R^3$ are as defined hereinabove.

This first step of this process can be effected by contacting compound (H) with an alkali metal metaperiodate (e.g. sodium metaperiodate) or lead tetraacetate preferably in an inert organic solvent. Typically, this process is conducted at temperatures in the range of about from 0° to 70° C., preferably 0° to 30° C. using about from 1.0 to 1.25 moles of alkali metal metaperiodate per mole of compound (H). Suitable solvents which can be used include, for example, tetrahydrofuran, methanol, benzene, toluene, water, and the like.

The second step can be effected by contacting compound J with triphenylethyl or triphenylpropyl phosphonium bromide and n-butyllithium, preferably in an inert organic solvent. Typically, this process is conducted at temperatures in the range of about from 0° to 70° C., preferably 20° to 30° C., using about from 0.8 to 3 moles of the bromide and about from 0.5 to 3 moles of butyllithium per mole of compound (J). Suitable inert organic solvents which can be used include, for example, tetrahydrofuran, benzene, hexane, dimethylsulfoxide, dimethoxyethane, and the like.

The preparation of the compound wherein $R'''$ is ethyl, $R^1$ is phenyl and $R^2$ and $R^3$ are each methyl, is also described in Tetrahedron Letters No. 35, pp. 3233–3236 (1978).

The compounds of Formula (Ia) wherein R is alkenyl having its unsaturation at the 2' position can be prepared by contacting the corresponding compound of Formula Ia but wherein R is formylmethyl [Helv. Chim. Acta 63, 1644 (1980)] with triphenylmethyl or triphenylethyl, phosphonium bromide and butyllithium in an inert organic solvent (e.g. tetrahydrofuran). This reaction can be conducted in the same manner as described for the second step hereinabove.

The compounds of Formula (Ia) wherein R is alkenyl having its unsaturation at the 3' position can be prepared by contacting the corresponding compound of Formula Ia but wherein R is p-toluenesulfonyloxymethyl with the Grignard reagent of allyl bromide or chloride preferably in an inert organic solvent (e.g., ethyl ether or tetrahydrofuran) and in the presence of a suitable catalyst in the same manner as the Grignard reaction as previously described above.

The compounds of Formula Ia wherein R is alkyl having 2 to 4 carbon atoms can also be made by hydrogenation of the corresponding R is alkenyl compound, for example, via hydrogenation in the presence of a suitable hydrogenation catalyst such as, for example, palladium on carbon.

The compounds of Formula (Ia) wherein one or both of $R^{2'}$ and/or $R^{3'}$ are hydrogen can be prepared from the corresponding $R^{2'}$ and $R^{3'}$ are each alkyl compound of Formula (Ia). This can be conveniently effected by contacting the $R^2$, $R^3$ alkyl compound of Formula (I) with an aldehyde having the appropriate $R^2$, $R^3$ substitution. For example, compound (Ia) wherein $R^{2'}$ and $R^{3'}$ are each hydrogen can be prepared by using paraformaldehyde and glacial acetic acid, followed by contact with a small amount of a strong acid (e.g. concentrated sulfuric acid), whereas the compound (Ia) wherein one of $R^{2'}$ and $R^{3'}$ is hydrogen and the other is methyl can be prepared by cleaving the 1,2-O-alkylidene group by acid hydrolysis and then contacting the cleaved product with acetaldehyde. Typically, the first step of this reaction where the 1,2-O-alkylidene group is cleaved by acid can be conveniently effected by mild acid hydrolysis, for example, by contacting the compound with aqueous trifluoroacetic acid, preferably at room temperature (about 20°–25° C.) for about 0.5–5 hours. Conveniently, the hydrolysis is conducted in a suitable inert organic solvent, such as for example, aqueous acetic acid, aqueous trifluoroacetic acid, aqueous hydrochloric acid and the like, and compatible mixtures thereof. The second step of this reaction is typically conducted at temperatures in the range of about from 25° C. to the boiling point of the aldehyde for about from 1 to 24 hours using about from 1 to 10 moles of aldehyde per mole of compound (Ia) in the presence of a catalytic amount of acid (e.g., concentrated sulfuric acid or p-toluenesulfonic acid) and a dehydrating agent such as anhydrous copper sulfate, or molecular sieves.

Variation in the $R^{2'}$, $R^{3'}$ alkyl substituents can also be effected in the compound (Ia) by cleaving the 1,2-O-alkylidene group by acid hydrolysis and then contacting the cleaved product with the appropriate ketone having the desired $R^{2'}$, $R^{3'}$ substitution in the presence of a dehydrating agent, as previously described with respect to the intermediates.

In the above-described processes, it is generally preferable to separate the respective products before proceeding with the next step in the reaction sequence unless expressly stated otherwise. These products can be recovered from their respective reaction product mixtures by any suitable separation and purification procedure, such as, for example, recrystallization and chromatography. Suitable separation and purification procedures are, for example, illustrated in the Examples set forth hereinbelow. Also generally it is preferred to use the appropriate isomer starting material having the same orientation as compound Ia. However, isomer mixtures of starting materials can also be used. In this case the product will be a mixture of compound Ia and its isomers. Compound Ia can then be separated from the isomer mixture or applied as a mixture.

Generally, the reactions described above are conducted as liquid phase reaction and hence pressure is generally not significant except as it affects temperature (boiling point) where reactions are conducted at reflux. Therefore, these reactions are generally conducted at pressures of from 300 to 3000 mm of mercury and conveniently are conducted at about atmospheric or ambient pressure. In the case of the hydrogenation described above, the hydrogenation is typically conducted by bubbling hydrogen through the substrate, dissolved in a solvent, or placing the substrate solution under hydrogen. Thus, the hydrogenation is typically conducted under a modest pressure, typically about from 800 to 3000 mm Hg.

It should also be appreciated that where typical or preferred process conditions (e.g., reaction temperatures, times, mol ratios of reactants, solvents, etc.) have been given, that other process conditions could also be used, although typically with poor yields or economies. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures, for example, by converting the isomer mixture to an acid derivative and reacting with an optically active base which will yield a mixture of optical salts, of the desired compound, which can be resolved by conventional procedures (e.g., crystallization) into the respective plus and minus optical salts.

Definitions

As used herein the following terms have the following meanings unless expressly stated to the contrary:

The term "lower alkyl" refers to both straight- and branched-chain alkyl groups having a total of from 1 through 4 carbon atoms and includes primary, secondary and tertiary alkyl groups. Typical lower alkyls include, for example, methyl, ethyl, n-propyl, isopropyl, n-butyl, t-butyl.

The term "lower alkenyl" refers to alkenyl groups having 2 through 4 carbon atoms and includes for example vinyl, 1-propenyl, 2-propenyl, 1-methylvinyl, 1-butenyl, 2-methylprop-1-enyl and the like.

The term "halo" refers to the group of fluoro, chloro, bromo and iodo.

The term "aryl" refers to aryl groups having 6 through 10 carbon atoms and includes, for example, phenyl, naphthyl, indenyl, and the like.

The term "substituted aryl" refers to aryl groups having 1 through 4 substituents independently selected from the group of lower alkyl, lower alkoxy and halo. Typical substituted aryl includes, for example, 2-fluorophenyl, 2-chlorophenyl, 2,6-dimethylphenyl, 2-methylphenyl, 2,4-dimethylphenyl, 2,5-dimethylphenyl, 2,4-dichlorophenyl, 2-methoxyphenyl and the like.

The term "room temperature" or "ambient temperature" refers to about 20°-25° C.

Utility

The compounds of Formula (Ia) exhibit both pre-emergence and post-emergence herbicide activity and exhibit especially good pre-emergence grass herbicide activity. Further, by proper reduction of the dosage, the compounds can be safely applied as selective pre-emergence grass herbicides to prevent or reduce the growth of grasses amongst broad leaf crops such as soybean. The preferred herbicidal compounds of Formula (I) are those wherein R is ethyl or propyl and especially the compound wherein R is ethyl.

Generally, for post-emergent applications, the herbicidal compounds are applied directly to the foliage or other plant parts. For pre-emergence applications, the herbicidal compounds are applied to the growing medium, or prospective growing medium, of the plant. The optimum amount of the herbicidal compound or composition will vary with the particular plant species, and the extent of part plant growth and the particular part of the plant which is contacted. The optimum dosage will also vary with the general location, or environment, of application (e.g., sheltered areas such as greenhouses compared to exposed areas such as fields), and type and degree of control desired. Generally, for both pre- and post-emergent control, the present compounds are applied at rates of about from 0.2 to 60 kg/ha, preferably about from 0.5 to 10 kg/ha.

Also, although in theory the compounds can be applied undiluted, in actual practice they are generally applied as a composition or formulation comprising an effective amount of the compound(s) and an acceptable carrier. An acceptable carrier (algriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having higher concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which can be used include, for example, water, organic solvents (e.g., hydrocarbons such as benzene, toluene, dimethylsulfoxide, kerosene, diesel fuel, fuel oil, petroleum naphtha, etc.), and the like.

Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound.

The composition can also contain various compatible adjuvants, stabilizers, conditioners, insecticides, fungicides, and if desired, other herbicidally active compounds.

The compounds of the present invention also exhibit plant growth regulating activity and especially root growth inhibition; foliage regrowth inhibition and crop enhancement. The former activity is useful where top growth is desirable. Foliage regrowth inhibition is desirable in cases such as the harvesting of cotton. In harvesting cotton, defoliants and desiccants are frequently used to remove the leaves of the cotton plant thus making the cotton more accessible. In such cases regrowth inhibitors are useful to inhibit the regrowth of leaves, before harvesting is completed. Crop enhancement is produced by pinching and increasing crop bearing branching in crops such as soy bean.

The present compounds of Formula (I) can be applied in pure form, but more pregmatically, as in the case of herbicide application, are applied in combination with a carrier. The same types of carriers as set forth hereinabove with respect to the herbicide compositions can also be used. Depending on the desired application, the plant growth regulating composition can also contain, or be applied in combination with other compatible ingredients such as desiccants, defoliants, surface-active agents, adjuvants, fungicides, insecticides and selective herbicides. Typically, the plant growth regulating composition will contain a total of about from 0.005 to 90 wt. %, of the compound(s) of Formula (Ia) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLE 1

1,2-O-Isopropylidene-a-D-xylofuranose

In this example 5 ml of concentrated 96 wt. % sulfuric acid; 100 g of anhydrous cupric sulfate and 50 g of D-xylose were sequentially added to 1 liter of acetone. The resulting mixture was then stirred vigorously for 25 hours at room temperature under anhydrous conditions. The solution was then filtered and washed with acetone. 16 ml of aqueous 15 N. Ammonium hydroxide was then added to the filtrate to render it basic. The filtrate was then filtered to remove solids and evaporated under reduced pressure. The above procedure was repeated, affording a combined yield of 123 g of crude product which was then distilled at 114°-118° C. under 3 mm mercury pressure affording 102 g of 1,2:3,5-di-O-isopropylidene-a-D-xylofuranose as a thick light yellow syrup. This product was confirmed by nmr analysis.

100 g of the above product was then warmed until molten in a round bottomed flask equipped with a mechanical stirrer and then cooled to room temperature and 550 ml of aqueous 0.2 wt. % hydrochloric acid were then added. The resulting mixture was stirred for 25 minutes at room temperature and then filtered. The filtrate was then neutralized to pH 7-8 by the controlled addition of sodium bicarbonate, and then evaporated to dryness under reduced pressure affording a yellow slurry. This slurry was dissolved in 500 ml of chloroform and then filtered. The filtrate was dried over anhydrous magnesium sulfate, and evaporated affording a yellow syrup. Examination of the syrup with thin layer chromatography showed that the reaction had only gone to about 50% completion. Accordingly, the syrup was redissolved in aqueous 0.2 wt. % hydrochloric acid and the procedure repeated affording 61.9 g of the title product.

Similarly, by following the same procedure by using the corresponding aldehyde or ketone in place of acetone, the following compounds can be respectively prepared:

1,2-O-ethylidene-a-D-xylofuranose;
1,2-O-(1-methylpropylidene)-a-D-xylofuranose;
1,2-O-(1-propylpentylidene)-a-D-xylofuranose; and
1,2-O-(1,2-dimethylpropylidene)-a-D-xylofuranose.

EXAMPLE 2

1,2-O-Isopropylidene-5-O-tosyl-a-D-xylofuranose

In this example a solution containing 68 g of paratoluenesulfonyl chloride dissolved in 124 ml of methylene chloride was slowly added dropwise to an anhydrous solution containing 61.9 g of 1,2-O-isopropylidene-a-D-xylofuranose in 310 ml of pyridine at 0° C. The mixture was stirred for one hour at 0° C. and then allowed to stand overnight at room temperature. The solution was then extracted three times with 200 ml of methylene chloride. The combined organic extracts were washed with cold dilute aqueous sulfuric acid to remove the pyridine, and then washed with water until neutral. The washed extract was then dried over magnesium sulfate and evaporated to dryness under vacuum affording 110 g of solid product. The solid product was then recrystallized twice from ethyl acetate affording the title compound, m.p. 134°-136.5° C.

Similarly, by following the same procedure using the corresponding products of Example 1 as starting materials, the following compounds can be respectfully prepared:

1,2-O-ethylidene-5-O-tosyl-a-D-xylofuranose;
1,2-O-(1-methylpropylidene)-5-O-tosyl-a-D-xylofuranose;
1,2-O-(1-propylpentylidene)-5-O-tosyl-a-D-xylofuranose; and
1,2-O-(1,2-dimethylpropylidene)-5-O-tosyl-a-D-xylofuranose.

EXAMPLE 3

1,2-O-Isopropylidene-5-Deoxy-5-C-Ethyl-a-D-xylofuranose

In this example, 0.1 mmoles of dilithium tetrachlorocuprate (Li$_2$CuCl$_4$) in 1 ml of tetrahydrofuran was added to 0.14 moles of ethyl magnesium bromide in 100 ml of ethyl ether and then cooled to −78° C. 6.9 g (0.02 moles) of 1,2-O-isopropylidene-5-O-tosyl-a-D-xylofuranose dissolved in 30 ml of tetrahydrofuran was then added. The resulting mixture was then stirred for 2 hours at room temperature and then refluxed overnight (about 12 hours). The mixture was then poured into a dilute aqueous sulfuric acid and ice mixture and then extracted three times with 50 ml of ethyl ether. The ether extracts were then combined and washed twice with 50 ml water, then dried over magnesium sulfate, and evaporated to dryness under a vacuum. The resulting residue was then crystallized from a mixture of ethyl ether and hexane affording 3.4 g of the title compound, m.p. 58°–60° C.

Similarly, by the following the same procedure but using the corresponding products of Example 2 as starting materials, the following compounds can be respectively prepared:
- 1,2-O-ethylidene-5-deoxy-5-C-ethyl-a-D-xylofuranose;
- 1,2-O-(1-methylpropylidene)-5-deoxy-5-C-ethyl-a-D-xylofuranose;
- 1,2-O-(1-propylpentylidene)-5-deoxy-5-C-ethyl-a-D-xylofuranose; and
- 1,2-O-(1,2-dimethylpropylidene)-5-deoxy-5-C-ethyl-a-D-xylofuranose.

Similarly, by following the same procedure but using methyl magnesium bromide in place of ethyl magnesium bromide, the following compounds can be respectively prepared:
- 1,2-O-isopropylidene-5-deoxy-5-C-methyl-a-D-xylofuranose;
- 1,2-O-ethylidene-5-deoxy-5-C-methyl-a-D-xylofuranose;
- 1,2-O-(1-methylpropylidene)-5-deoxy-5-C-methyl-a-D-xylofuranose;
- 1,2-O-(1-propylpentylidene)-5-deoxy-5-C-methyl-a-D-xylofuranose; and
- 1,2-O-(1,2-dimethylpropylidene)-5-deoxy-5-C-methyl-a-D-xylofuranose.

Similarly, by following the same procedure but using propyl magnesium bromide and isopropyl magnesium bromide respectively in place of ethyl magnesium bromide, the corresponding 5-C-propyl and 5-C-isopropyl homologs of the above compounds can be respectively prepared.

EXAMPLE 4

1,2-O-isopropylidene-3-O-benzyl-5-deoxy-5-C-ethyl-a-D-xylofuranose

In this example 1.15 g (0.024 mole) of 50 wt. % sodium hydride was slowly added to a solution containing 4.0 g of 1,2-O-isopropylidene-5-deoxy-5-C-ethyl-a-D-xylofuranose in 20 ml of tetrahydrofuran, under a nitrogen atmosphere, at room temperature. After 15 minutes, 0.3 g of tetrabutyl ammonium iodide and 4.1 g (0.024 moles) of benzyl bromide were added and the reaction mixture was then stirred overnight at room temperature. The reaction mixture was then concentrated by evaporation under vacuum and then 100 ml of water and 100 ml of methylene chloride were added. The resulting organic layer was then separated and washed twice with 100 ml portions of water and then dried over anhydrous magnesium sulfate and concentrated by vacuum evaporation. The resulting concentrated liquid was then dissolved in 100 ml of acetonitrile and then washed twice with 20 ml of hexane to remove mineral oil. The liquid was then evaporated under vacuum affording a liquid which was then distilled at 152°–155° C. under 1 mm of mercury pressure affording 3.4 g of the title compound.

Similarly, by following the same procedure but using the corresponding products of Example 3 as starting materials, the following compounds can be respectively prepared:
- 1,2-O-ethylidene-3-O-benzyl-5-deoxy-5-C-ethyl-a-D-xylofuranose;
- 1,2-O-(1-methylpropylidene)-3-O-benzyl-5-deoxy-5-C-ethyl-a-D-xylofuranose;
- 1,2-O-(1-propylpentylidene)-3-O-benzyl-5-deoxy-5-C-ethyl-a-D-xylofuranose; and
- 1,2-O-(1,2-dimethylpropylidene)-3-O-benzyl-5-deoxy-5-C-ethyl-a-D-xylofuranose;
- 1,2-O-isopropylidene-3-O-benzyl-5-deoxy-5-C-methyl-a-D-xylofuranose;
- 1,2-O-ethylidene-3-O-benzyl-5-deoxy-5-C-methyl-a-D-xylofuranose;
- 1,2-O-(1-methylpropylidene)-3-O-benzyl-5-deoxy-5-C-methyl-a-D-xylofuranose;
- 1,2-O-(1-propylpentylidene)-3-O-benzyl-5-deoxy-5-C-methyl-a-D-xylofuranose;
- 1,2-O-(1,2-dimethylpropylidene)-3-O-benzyl-5-deoxy-5-C-methyl-a-D-xylofuranose;
- 1,2-O-isopropylidene-3-O-benzyl-5-deoxy-5-C-propyl-a-D-xylofuranose;
- 1,2-O-ethylidene-3-O-benzyl-5-deoxy-5-propyl-a-D-xylofuranose;
- 1,2-O-(1-methylpropylidene)-3-O-benzyl-5-deoxy-5-C-propyl-a-D-xylofuranose;
- 1,2-O-(1-propylpentylidene)-3-O-benzyl-5-deoxy-5-C-propyl-a-D-xylofuranose;
- 1,2-O-(1,2-dimethylpropylidene)-3-O-benzyl-5-deoxy-5-C-propyl-a-D-xylofuranose;
- 1,2-O-isopropylidene-3-O-benzyl-5-deoxy-5-C-isopropyl-a-D-xylofuranose;
- 1,2-O-ethylidene-3-O-benzyl-5-deoxy-5-C-isopropyl-a-D-xylofuranose;
- 1,2-O-(1-methylpropylidene)-3-O-benzyl-5-deoxy-5-C-isopropyl-a-D-xylofuranose;
- 1,2-O-(1-propylpentylidene)-3-O-benzyl-5-deoxy-5-C-isopropyl-a-D-xylofuranose;
- 1,2-O-(1,2-dimethylpropylidene)-3-O-benzyl-5-deoxy-5-C-isopropyl-a-D-xylofuranose.

Similarly, by following the same procedure but using 2-chlorobenzyl bromide in place of benzyl bromide, the following compounds can be respectively prepared:
- 1,2-O-isopropylidene-3-O-(2'-chlorobenzyl)-5-deoxy-5-C-ethyl-a-D-xylofuranose;
- 1,2-O-ethylidene-3-O-(2'-chlorobenzyl)-5-deoxy-5-C-ethyl-a-D-xylofuranose;
- 1,2-O-(1-methylpropylidene)-3-O-(2'-chlorobenzyl)-5-deoxy-5-C-ethyl-a-D-xylofuranose;
- 1,2-O-(1-propylpentylidene)-3-O-(2'-chlorobenzyl)-5-deoxy-5-C-ethyl-a-D-xylofuranose; and
- 1,2-O-(1,2-dimethylpropylidene)-3-O-(2'-chlorobenzyl)-5-deoxy-5-C-ethyl-a-D-xylofuranose;
- 1,2-O-isopropylidene-3-O-(2'-chlorobenzyl)-5-deoxy-5-C-methyl-a-D-xylofuranose;

1,2-O-ethylidene-3-O-(2'-chlorobenzyl)-5-deoxy-5-C-methyl-a-D-xylofuranose;
1,2-O-(1-methylpropylidene)-3-O-(2'-chlorobenzyl)-5-deoxy-5-C-methyl-a-D-xylofuranose;
1,2-O-(1-propylpentylidene)-3-O-(2'-chlorobenzyl)-5-deoxy-5-C-methyl-a-D-xylofuranose;
1,2-O-(1,2-dimethylpropylidene)-3-O-(2'-chlorobenzyl)-5-deoxy-5-C-methyl-a-D-xylofuranose;
1,2-O-isopropylidene-3-O-(2'-chlorobenzyl)-5-deoxy-5-C-propyl-a-D-xylofuranose;
1,2-O-ethylidene-3-O-(2'-chlorobenzyl)-5-deoxy-5-C-propyl-a-D-xylofuranose;
1,2-O-(1-methylpropylidene)-3-O-(2'-chlorobenzyl)-5-deoxy-5-C-propyl-a-D-xylofuranose;
1,2-O-(1-propylpentylidene)-3-O-(2'-chlorobenzyl)-5-deoxy-5-C-propyl-a-D-xylofuranose;
1,2-O-(1,2-dimethylpropylidene)-3-O-(2'-chlorobenzyl)-5-deoxy-5-C-propyl-a-D-xylofuranose;
1,2-O-isopropylidene-3-O-(2'-chlorobenzyl)-5-deoxy-5-C-isopropyl-a-D-xylofuranose;
1,2-O-ethylidene-3-O-(2'-chlorobenzyl)-5-deoxy-5-C-isopropyl-a-D-xylofuranose;
1,2-O-(1-methylpropylidene)-3-O-(2'-chlorobenzyl)-5-deoxy-5-C-isopropyl-a-D-xylofuranose;
1,2-O-(1-propylpentylidene)-3-O-(2'-chlorobenzyl)-5-deoxy-5-C-isopropyl-a-D-xylofuranose;
1,2-O-(1,2-dimethylpropylidene)-3-O-(2'-chlorobenzyl)-5-deoxy-5-C-isopropyl-a-D-xylofuranose.

Similarly, by following the same procedure but respectively using 2-fluorobenzyl bromide; 2-trifluoromethylbenzyl bromide; 2,6-dimethylbenzyl bromide; 2-methoxybenzyl bromide; and 2-naphthamethyl bromide; the following compounds can be respectively prepared:

1,2-O-isopropylidene-3-O-(2'-fluorobenzyl)-5-deoxy-5-C-ethyl-a-D-xylofuranose;
1,2-O-ethylidene-3-O-(2'-fluorobenzyl)-5-deoxy-5-C-ethyl-a-D-xylofuranose;
1,2-O-(1-methylpropylidene)-3-O-(2'-fluorobenzyl)-5-deoxy-5-C-ethyl-a-D-xylofuranose;
1,2-O-(1-propylpentylidene)-3-O-(2'-fluorobenzyl)-5-deoxy-5-C-ethyl-a-D-xylofuranose;
1,2-O-(1,2-dimethylpropylidene)-3-O-(2'-fluorobenzyl)-5-deoxy-5-C-ethyl-a-D-xylofuranose;
1,2-O-isopropylidene-3-O-(2'-fluorobenzyl)-5-deoxy-5-C-methyl-a-D-xylofuranose;
1,2-O-ethylidene-3-O-(2'-fluorobenzyl)-5-deoxy-5-C-methyl-a-D-xylofuranose;
1,2-O-(1-methylpropylidene)-3-O-(2'-fluorobenzyl)-5-deoxy-5-C-methyl-a-D-xylofuranose;
1,2-O-(1-propylpentylidene)-3-O-(2'-fluorobenzyl)-5-deoxy-5-C-methyl-a-D-xylofuranose;
1,2-O-(1,2-dimethylpropylidene)-3-O-(2'-fluorobenzyl)-5-deoxy-5-C-methyl-a-D-xylofuranose;
1,2-O-isopropylidene-3-O-(2'-fluorobenzyl)-5-deoxy-5-C-propyl-a-D-xylofuranose;
1,2-O-ethylidene-3-O-(2'-fluorobenzyl)-5-deoxy-5-C-propyl-a-D-xylofuranose;
1,2-O-(1-methylpropylidene)-3-O-(2'-fluorobenzyl)-5-deoxy-5-C-propyl-a-D-xylofuranose;
1,2-O-(1-propylpentylidene)-3-O-(2'-fluorobenzyl)-5-deoxy-5-C-propyl-a-D-xylofuranose;
1,2-O-(1,2-dimethylpropylidene)-3-O-(2'-fluorobenzyl)-5-deoxy-5-C-propyl-a-D-xylofuranose;
1,2-O-isopropylidene-3-O-(2'-fluorobenzyl)-5-deoxy-5-C-isopropyl-a-D-xylofuranose;
1,2-O-ethylidene-3-O-(2'-fluorobenzyl)-5-deoxy-5-C-isopropyl-a-D-xylofuranose;
1,2-O-(1-methylpropylidene)-3-O-(2'-fluorobenzyl)-5-deoxy-5-C-isopropyl-a-D-xylofuranose;
1,2-O-(1-propylpentylidene)-3-O-(2'-fluorobenzyl)-5-deoxy-5-C-isopropyl-a-D-xylofuranose;
1,2-O-(1,2-dimethylpropylidene)-3-O-(2'-fluorobenzyl)-5-deoxy-5-C-isopropyl-a-D-xylofuranose;
1,2-O-isopropylidene-3-O-(2'-trifluoromethylbenzyl)-5-deoxy-5-C-ethyl-a-D-xylofuranose;
1,2-O-ethylidene-3-O-(2'-trifluoromethylbenzyl)-5-deoxy-5-C-ethyl-a-D-xylofuranose;
1,2-O-(1-methylpropylidene)-3-O-(2'-trifluoromethylbenzyl)-5-deoxy-5-C-ethyl-a-D-xylofuranose;
1,2-O-(1-propylpentylidene)-3-O-(2'-trifluoromethylbenzyl)-5-deoxy-5-C-ethyl-a-D-xylofuranose;
1,2-O-(1,2-dimethylpropylidene)-3-O-(2'-trifluoromethylbenzyl)-5-deoxy-5-C-ethyl-a-D-xylofuranose;
1,2-O-isopropylidene-3-O-(2'-trifluoromethylbenzyl)-5-deoxy-5-C-methyl-a-D-xylofuranose;
1,2-O-ethylidene-3-O-(2'-trifluoromethylbenzyl)-5-deoxy-5-C-methyl-a-D-xylofuranose;
1,2-O-(1-methylpropylidene)-3-O-(2'-trifluoromethylbenzyl)-5-deoxy-5-C-methyl-a-D-xylofuranose;
1,2-O-(1-propylpentylidene)-3-O-(2'-trifluoromethylbenzyl)-5-deoxy-5-C-methyl-a-D-xylofuranose;
1,2-O-(1,2-dimethylpropylidene)-3-O-(2'-trifluoromethylbenzyl)-5-deoxy-5-C-methyl-a-D-xylofuranose;
1,2-O-isopropylidene-3-O-(2'-trifluoromethylbenzyl)-5-deoxy-5-C-propyl-a-D-xylofuranose;
1,2-O-ethylidene-3-O-(2'-trifluoromethylbenzyl)-5-deoxy-5-C-propyl-a-D-xylofuranose;
1,2-O-(1-methylpropylidene)-3-O-(2'-trifluoromethylbenzyl)-5-deoxy-5-C-propyl-a-D-xylofuranose;
1,2-O-(1-propylpentylidene)-3-O-(2'-trifluoromethylbenzyl)-5-deoxy-5-C-propyl-a-D-xylofuranose;
1,2-O-(1,2-dimethylpropylidene)-3-O-(2'-trifluoromethylbenzyl)-5-deoxy-5-C-propyl-a-D-xylofuranose;
1,2-O-isopropylidene-3-O-(2'-trifluoromethylbenzyl)-5-deoxy-5-C-isopropyl-a-D-xylofuranose;
1,2-O-ethylidene-3-O-(2'-trifluoromethylbenzyl)-5-deoxy-5-C-isopropyl-a-D-xylofuranose;
1,2-O-(1-methylpropylidene)-3-O-(2'-trifluoromethylbenzyl)-5-deoxy-5-C-isopropyl-a-D-xylofuranose;
1,2-O-(1-propylpentylidene)-3-O-(2'-trifluoromethylbenzyl)-5-deoxy-5-C-isopropyl-a-D-xylofuranose;
1,2-O-(1,2-dimethylpropylidene)-3-O-(2'-trifluoromethylbenzyl)-5-deoxy-5-C-isopropyl-a-D-xylofuranose;
1,2-O-isopropylidene-3-O-(2',6'-dimethylbenzyl)-5-deoxy-5-C-ethyl-a-D-xylofuranose;
1,2-O-ethylidene-3-O-(2',6'-dimethylbenzyl)-5-deoxy-5-C-ethyl-a-D-xylofuranose;
1,2-O-(1-methylpropylidene)-3-O-(2',6'-dimethylbenzyl)-5-deoxy-5-C-ethyl-a-D-xylofuranose;
1,2-O-(1-propylpentylidene)-3-O-(2',6'-dimethylbenzyl)-5-deoxy-5-C-ethyl-a-D-xylofuranose;
1,2-O-(1,2-dimethylpropylidene)-3-O-(2',6'-dimethylbenzyl)-5-deoxy-5-C-ethyl-a-D-xylofuranose;
1,2-O-isopropylidene-3-O-(2',6'-dimethylbenzyl)-5-deoxy-5-C-methyl-a-D-xylofuranose;
1,2-O-ethylidene-3-O-(2',6'-dimethylbenzyl)-5-deoxy-5-C-methyl-a-D-xylofuranose;
1,2-O-(1-methylpropylidene)-3-O-(2',6'-dimethylbenzyl)-5-deoxy-5-C-methyl-a-D-xylofuranose;
1,2-O-(1-propylpentylidene)-3-O-(2',6'-dimethylbenzyl)-5-deoxy-5-C-methyl-a-D-xylofuranose;

1,2-O-(1,2-dimethylpropylidene)-3-O-(2',6'-dimethylbenzyl)-5-deoxy-5-C-methyl-a-D-xylofuranose;
1,2-O-isopropylidene-3-O-(2',6'-dimethylbenzyl)-5-deoxy-5-C-propyl-a-D-xylofuranose;
1,2-O-ethylidene-3-O-(2',6'-dimethylbenzyl)-5-deoxy-5-C-propyl-a-D-xylofuranose;
1,2-O-(1-methylpropylidene)-3-O-(2',6'-dimethylbenzyl)-5-deoxy-5-C-propyl-a-D-xylofuranose;
1,2-O-(1-propylpentylidene)-3-O-(2',6'-dimethylbenzyl)-5-deoxy-5-C-propyl-a-D-xylofuranose;
1,2-O-(1,2-dimethylpropylidene)-3-O-(2',6'-dimethylbenzyl)-5-deoxy-5-C-propyl-a-D-xylofuranose;
1,2-O-isopropylidene-3-O-(2',6'-dimethylbenzyl)-5-deoxy-5-C-isopropyl-a-D-xylofuranose;
1,2-O-ethylidene-3-O-(2',6'-dimethylbenzyl)-5-deoxy-5-C-isopropyl-a-D-xylofuranose;
1,2-O-(1-methylpropylidene)-3-O-(2',6'-dimethylbenzyl)-5-deoxy-5-C-isopropyl-a-D-xylofuranose;
1,2-O-(1-propylpentylidene)-3-O-(2',6'-dimethylbenzyl)-5-deoxy-5-C-isopropyl-a-D-xylofuranose;
1,2-O-(1,2-dimethylpropylidene)-3-O-(2',6'-dimethylbenzyl)-5-deoxy-5-C-isopropyl-a-D-xylofuranose;
1,2-O-isopropylidene-3-O-(2'-methoxybenzyl)-5-deoxy-5-C-ethyl-a-D-xylofuranose;
1,2-O-ethylidene-3-O-(2'-methoxybenzyl)-5-deoxy-5-C-ethyl-a-D-xylofuranose;
1,2-O-(1-methylpropylidene)-3-O-(2'-methoxybenzyl)-5-deoxy-5-C-ethyl-a-D-xylofuranose;
1,2-O-(1-propylpentylidene)-3-O-(2'-methoxybenzyl)-5-deoxy-5-C-ethyl-a-D-xylofuranose; and
1,2-O-(1,2-dimethylpropylidene)-3-O-(2'-methoxybenzyl)-5-deoxy-5-C-ethyl-a-D-xylofuranose;
1,2-O-isopropylidene-3-O-(2'-methoxybenzyl)-5-deoxy-5-C-methyl-a-D-xylofuranose;
1,2-O-ethylidene-3-O-(2'-methoxybenzyl)-5-deoxy-5-C-methyl-a-D-xylofuranose;
1,2-O-(1-methylpropylidene)-3-O-(2'-methoxybenzyl)-5-deoxy-5-C-methyl-a-D-xylofuranose;
1,2-O-(1-propylpentylidene)-3-O-(2'-methoxybenzyl)-5-deoxy-5-C-methyl-a-D-xylofuranose;
1,2-O-(1,2-dimethylpropylidene)-3-O-(2'-methoxybenzyl)-5-deoxy-5-C-methyl-a-D-xylofuranose;
1,2-O-isopropylidene-3-O-(2'-methoxybenzyl)-5-deoxy-5-C-propyl-a-D-xylofuranose;
1,2-O-ethylidene-3-O-(2'-methoxybenzyl)-5-deoxy-5-C-propyl-a-D-xylofuranose;
1,2-O-(1-methylpropylidene)-3-O-(2'-methoxybenzyl)-5-deoxy-5-C-propyl-a-D-xylofuranose;
1,2-O-(1-propylpentylidene)-3-O-(2'-methoxybenzyl)-5-deoxy-5-C-propyl-a-D-xylofuranose;
1,2-O-(1,2-dimethylpropylidene)-3-O-(2'-methoxybenzyl)-5-deoxy-5-C-propyl-a-D-xylofuranose;
1,2-O-isopropylidene-3-O-(2'-methoxybenzyl)-5-deoxy-5-C-isopropyl-a-D-xylofuranose;
1,2-O-ethylidene-3-O-(2'-methoxybenzyl)-5-deoxy-5-C-isopropyl-a-D-xylofuranose;
1,2-O-(1-methylpropylidene)-3-O-(2'-methoxybenzyl)-5-deoxy-5-C-isopropyl-a-D-xylofuranose;
1,2-O-(1-propylpentylidene)-3-O-(2'-methoxybenzyl)-5-deoxy-5-C-isopropyl-a-D-xylofuranose;
1,2-O-(1,2-dimethylpropylidene)-3-O-(2'-methoxybenzyl)-5-deoxy-5-C-isopropyl-a-D-xylofuranose;
1,2-O-isopropylidene-3-O-(2'-naphthamethyl)-5-deoxy-5-C-ethyl-a-D-xylofuranose;
1,2-O-ethylidene-3-O-(2'-naphthamethyl)-5-deoxy-5-C-ethyl-a-D-xylofuranose;
1,2-O-(1-methylpropylidene)-3-O-(2'-naphthamethyl)-5-deoxy-5-C-ethyl-a-D-xylofuranose;
1,2-O-(1-propylpentylidene)-3-O-(2'-naphthamethyl)-5-deoxy-5-C-ethyl-a-D-xylofuranose; and
1,2-O-(1,2-dimethylpropylidene)-3-O-(2'-naphthamethyl)-5-deoxy-5-C-ethyl-a-D-xylofuranose;
1,2-O-isopropylidene-3-O-(2'-naphthamethyl)-5-deoxy-5-C-methyl-a-D-xylofuranose;
1,2-O-ethylidene-3-O-ethylidene-3-O-(2'-naphthamethyl)-5-deoxy-5-C-methyl-a-D-xylofuranose;
1,2-O-(1-methylpropylidene)-3-O-(2'-naphthamethyl)-5-deoxy-5-C-methyl-a-D-xylofuranose;
1,2-O-(1-propylpentylidene)-3-O-(2'-naphthamethyl)-5-deoxy-5-C-methyl-a-D-xylofuranose;
1,2-O-(1,2-dimethylpropylidene)-3-O-(2'-naphthamethyl)-5-deoxy-5-C-methyl-a-D-xylofuranose;
1,2-O-isopropylidene-3-O-(2'-naphthamethyl)-5-deoxy-5-C-propyl-a-D-xylofuranose;
1,2-O-ethylidene-3-O-(2'-naphthamethyl)-5-deoxy-5-C-propyl-a-D-xylofuranose;
1,2-O-(1-methylpropylidene)-3-O-(2'-naphthamethyl)-5-deoxy-5-C-propyl-a-D-xylofuranose;
1,2-O-(1-propylpentylidene)-3-O-(2'-naphthamethyl)-5-deoxy-5-C-propyl-a-xylofuranose;
1,2-O-(1,2-dimethylpropylidene)-3-O-(2'-naphthamethyl)-5-deoxy-5-C-propyl-a-D-xylofuranose;
1,2-O-isopropylidene-3-O-(2'-naphthamethyl)-5-deoxy-5-C-isopropyl-a-D-xylofuranose;
1,2-O-ethylidene-3-O-(2'-naphthamethyl)-5-deoxy-5-C-isopropyl-a-D-xylofuranose;
1,2-O-(1-methylpropylidene)-3-O-(2'-naphthamethyl)-5-deoxy-5-C-isopropyl-a-D-xylofuranose;
1,2-O-(1-propylpentylidene)-3-O-(2'-naphthamethyl)-5-deoxy-5-C-isopropyl-a-D-xylofuranose;
1,2-O-(1,2-dimethylpropylidene)-3-O-(2'-naphthamethyl)-5-deoxy-5-C-isopropyl-a-D-xylofuranose.

Similarly, by following the same procedure but respectively replacing benzyl bromide with 2-methylbenzyl bromide; 3-methylbenzyl bromide; 2,6-dichlorobenzyl bromide; 2,3,4,6-tetrafluorobenzyl bromide; 2-bromo-4-methylbenzyl bromide; 2,3-dimethyl-4-methoxybenzyl bromide; 2,4-dimethylbenzyl bromide; 2,5-dimethylbenzyl bromide; 2,4-dibutylbenzyl bromide; 3,4-diethoxybenzyl bromide; 2-chloro-4-iodobenzyl bromide, 2-methyl-5-methoxybenzyl bromide and 6-methyl-2-naphthamethyl bromide, the corresponding 2-methylbenzyl; 3-methyl bromide, the corresponding 2-methylbenzyl; 3-methylbenzyl; 2,6-dichlorobenzyl; 2,3,4,6-tetrafluorobenzyl; 2-bromo-4-methyl benzyl; 2,3-dimethyl-4-methoxybenzyl; 2,4-dimethylbenzyl; 2,5-dimethylbenzyl; 2,4-dibutylbenzyl; 3,4-diethoxybenzyl; 2-chloro-4-iodobenzyl; 2-methyl-5-ethoxybenzyl; and 6-ethyl-2-naphthamethyl analogs of each of the above compounds can be respectively prepared.

EXAMPLE 5

1,2-O-isopropylidene-5-deoxy-5-iodo-a-D-xylofuranose

In this example 25 g (170 mmoles) of sodium iodide was added to a solution containing 34 g of 1,2-O-isopropylidene-5-O-tosyl-a-D-xylofuranose dissolved in 250 ml of methyl ethyl ketone and then refluxed, with stirring, for 24 hours. The reaction mixture was allowed to cool and then filtered. The filtrate was then evaporated affording an oil concentrate which was then dissolved in 150 ml of chloroform and then washed with 100 ml of aqueous sodium thiosulfate solution and then washed three times with 150 ml of water. The chloroform layer was dried over anhydrous magnesium sulfate and then evaporated under vacuum affording the title compound which was crystallized from ether-hexane, m.p. 102°–105° C.

Similarly, by following the same procedure using the corresponding products prepared in Example 2, the following compounds can be respectively prepared:
- 1,2-O-ethylidene-5-deoxy-5-iodo-a-D-xylofuranose;
- 1,2-O-(1-methylpropylidene)-5-deoxy-5-iodo-a-D-xylofuranose;
- 1,2-O-(1-propylpentylidene)-5-deoxy-5-iodo-a-D-xylofuranose; and
- 1,2-O-(1,2-dimethylpropylidene)-5-deoxy-5-iodo-a-D-xylofuranose.

EXAMPLE 6

1,2-O-isopropylidene-5-deoxy-a-D-xylofuranose

In this example, a reaction mixture containing 2.0 g (10 mmoles) of 1,2-O-isopropylidene-5-deoxy-5-iodo-a-D-xylofuranose, 1.5 g (15 mmoles) of triethylamine and 0.1 g of platinum oxide in 30 ml of methanol was hydrogenated at room temperature under a hydrogen pressure of 10 psig. Hydrogenation was continued until no further absorption of hydrogen was observed (approximately 1 hour). The reaction mixture was then filtered through diatomaceous earth. The resulting filtrate was evaporated affording the title compound as an off-white solid. This solid was then recrystallized from a mixture of ethyl ether and hexane.

Similarly by following the same procedure but respectively using the products of Example 5 as starting materials, the following compounds can be respectively prepared:
- 1,2-O-ethylidene-5-deoxy-a-D-xylofuranose;
- 1,2-O-(1-methylpropylidene)-5-deoxy-a-D-xylofuranose;
- 1,2-O-(1-propylpentylidene)-5-deoxy-a-D-xylofuranose; and
- 1,2-O-(1,2-dimethylpropylidene)-5-deoxy-a-D-xylofuranose.

EXAMPLE 7

1,2-O-isopropylidene-3-O-benzyl-5-deoxy-a-D-xylofuranose

In this example, 1.15 g (0.024 moles) of sodium hydride, in the form of a 50 wt. % mixture with mineral oil, was slowly added under a nitrogen atmosphere to a solution containing 3.5 g of 1,2-O-isopropylidene-5-deoxy-a-D-xylofuranose in 20 ml of tetrahydrofuran at room temperature. After 15 minutes, 0.3 g of tetrabutyl ammonium iodide and 4.1 g (0.024 moles) of benzyl bromide were added. The resulting mixture was stirred overnight at room temperature. The reaction mixture was then concentrated by evaporation under reduced pressure. 100 ml of water and 100 ml of methylene chloride were then added to the concentrate. The organic layer was separated and washed twice with water and dried by using anhydrous magnesium sulfate and concentrated by evaporation affording a yellow liquid. This liquid was then dissolved in 100 ml of acetonitrile and washed twice with 15 ml of hexane to remove mineral oil. The acetonitrile layer was separated and evaporated affording a liquid which was then distilled at 132°–135° C. and 0.5 mm Hg affording 3.6 g of the title compound as a colorless liquid.

Similarly, by following the same procedure using the corresponding products of Example 6 as starting materials, the following compounds can be respectively prepared:
- 1,2-O-ethylidene-3-O-benzyl-5-deoxy-a-D-xylofuranose;
- 1,2-O-(1-methylpropylidene)-3-O-benzyl-5-deoxy-a-D-xylofuranose;
- 1,2-O-(1-propylpentylidene)-3-O-benzyl-5-deoxy-a-D-xylofuranose; and
- 1,2-O-(1,2-dimethylpropylidene)-3-O-benzyl-5-deoxy-a-D-xylofuranose.

Similarly, by following the same procedure but using 2-chlorobenzyl bromide in place of benzyl bromide the following compounds can be respectively prepared:
- 1,2-O-isopropylidene-3-O-(2'-chlorobenzyl)-5-deoxy-a-D-xylofuranose;
- 1,2-O-methylene-3-O-(2'-chlorobenzyl)-5-deoxy-a-D-xylofuranose;
- 1,2-O-ethylidene-3-O-(2'-chlorobenzyl)-5-deoxy-a-D-xylofuranose;
- 1,2-O-(1-methylpropylidene)-3-O-(2'-chlorobenzyl)-5-deoxy-a-D-xylofuranose;
- 1,2-O-(1-propylpentylidene)-3-O-(2'-chlorobenzyl)-5-deoxy-a-D-xylofuranose; and
- 1,2-O-(1,2-dimethylpropylidene)-3-O-(2'-chlorobenzyl)-5-deoxy-a-D-xylofuranose.

Similarly, by following the same procedure but using 2-fluorobenzyl bromide in place of benzyl bromide the following compounds can be respectively prepared:
- 1,2-O-isopropylidene-3-O-(2'-fluorobenzyl)-5-deoxy-a-D-xylofuranose;
- 1,2-O-methylene-3-O-(2'-fluorobenzyl)-5-deoxy-a-D-xylofuranose;
- 1,2-O-ethylidene-3-O-(2'-fluorobenzyl)-5-deoxy-a-D-xylofuranose;
- 1,2-O-(1-methylpropylidene)-3-O-(2'-fluorobenzyl)-5-deoxy-a-D-xylofuranose;
- 1,2-O-(1-propylpentylidene)-3-O-(2'-fluorobenzyl)-5-deoxy-a-D-xylofuranose; and
- 1,2-O-(1,2-dimethylpropylidene)-3-O-(2'-fluorobenzyl)-5-deoxy-a-D-xylofuranose.

Similarly, by following the same procedure but respectively replacing benzyl bromide with 2-methylbenzyl bromide; 3-methylbenzyl bromide; 2,6-dichlorobenzyl bromide; 2,3,4,6-tetrafluorobenzyl bromide; 2-bromo-4-methylbenzyl bromide; 2,3-dimethyl-4-methoxybenzyl bromide; 2,4-dimethylbenzyl bromide; 2,5-dimethylbenzyl bromide; 2,4-dibutylbenzyl bromide; 3,4-diethoxybenzyl bromide; 2-chloro-4-iodobenzyl bromide and 2-methyl-5-methoxybenzyl bromide and 6-ethyl-2-naphthamethyl bromide, the corresponding 2-methylbenzyl; 3-methylbenzyl; 2,6-dichlorobenzyl; 2,3,4,6-tetrafluorobenzyl; 2-bromo-4-methyl benzyl; 2,3-dimethyl-4-methoxybenzyl; 2,4-dimethylbenzyl; 2,5-dimethylbenzyl; 2,4-dibutylbenzyl; 3,4-diethoxybenzyl; 2-chloro-4-iodobenzyl; 2-methyl-5-ethoxybenzyl; and 6-ethyl-2-naphthamethyl analogs of each of the above compounds are respectively prepared.

EXAMPLE 8

1,2:5,6-di-O-isopropylidene-a-D-glucofuranose

In this example, 125 g of powdered D-glucose is added to a stirred solution of 120 ml of concentrated 96 wt.% sulfuric acid in 3 liters of acetone and the mixture is stirred vigorously at room temperature overnight. The reaction mixture is cooled to 10° C. and gaseous ammonia is bubbled keeping the temperature below 25° C. Solids are filtered off and the filtrate is concentrated under reduced pressure. The residue is treated with 1 liter of water and extracted three times with 300 ml of methylene chloride. The methylene chloride extracts are combined, washed with water, dried with anhydrous magnesium sulfate, and concentrated to give a white crystalline residue of crude 1,2:5,6-di-O-isopropylidene-a-D-glucofuranose.

Similarly, by following the same procedure but using the corresponding ketone in place of acetone, the following compounds can be respectively prepared:

1,2:5,6-di-O-(1-methylpropylidene)-a-D-glucofuranose;
1,2:5,6-di-O-(1-ethylpropylidene)-a-D-glucofuranose; and
1,2:5,6-di-O-(1-propylbutylidene)-a-D-glucofuranose.

EXAMPLE 9

1,2:5,6-di-O-isopropylidene-3-O-(2'-chlorobenzyl)-a-D-glucofuranose

In this example 4.9 g (0.1 moles) of sodium hydride in the form of a 50 wt. % mixture with mineral oil was slowly added under an atmosphere of nitrogen to a cooled solution containing 26 g of 1,2:5,6-di-O-isopropylidene-a-D-glucofuranose in 75 ml of tetrahydrofuran. 2 g of benzyl triethyl ammonium chloride was then added to this mixture and then 16.1 g (0.1 moles) of 2-chlorobenzyl chloride was added. The reaction mixture was then stirred overnight (about 12 hours) at room temperature. The reaction mixture was concentrated by evaporation under reduced pressure affording a viscous mixture which was then dissolved in 200 ml of petroleum ether and washed three times with 100 ml water, then dried over anhydrous magnesium sulfate and evaporated under vacuum. The resulting liquid residue was distilled under vacuum to remove unreacted 2-chlorobenzyl chloride affording the title compound as a liquid.

Similarly, by following the same procedure by respectively using the other products of Example 8 as starting materials, the following compounds can be respectively prepared:

1,2:5,6-di-O-(1-methylpropylidene)-3-O-(2'-chlorobenzyl)-a-D-glucofuranose;
1,2:5,6-di-O-(1-ethylpropylidene)-3-O-(2'-chlorobenzyl)-a-D-glucofuranose; and
1,2:5,6-di-O-(1-propylbutylidene)-3-O-(2'-chlorobenzyl)-a-D-glucofuranose.

Similarly, by following the same procedure but respectively using benzyl chloride; 2-fluorobenzyl chloride; 3-hexylbenzyl chloride; 3-bromobenzylchloride; 4-methoxybenzyl chloride; 2-fluoro-4-methylbenzyl chloride; and 2,3,4,5-tetramethylbenzyl chloride, the following compounds can be respectively prepared:

1,2:5,6-di-O-isopropylidene-3-O-benzyl-a-D-glucofuranose;
1,2:5,6-di-O-(1-methylpropylidene)-3-O-benzyl-a-D-glucofuranose;
1,2:5,6-di-O-(1-ethylpropylidene)-3-O-benzyl-a-D-glucofuranose; and
1,2:5,6-di-O-(1-propylbutylidene)-3-O-benzyl-a-D-glucofuranose;
1,2:5,6-di-O-isopropylidene-3-O-(2'-fluorobenzyl)-a-D-glucofuranose;
1,2:5,6-di-O-(1-methylpropylidene)-3-O-(2'-fluorobenzyl)-a-D-glucofuranose;
1,2:5,6-di-O-(1-ethylpropylidene)-3-O-(2'-fluorobenzyl)-a-D-glucofuranose; and
1,2:5,6-di-O-(1-propylbutylidene)-3-O-(2'-fluorobenzyl)-a-D-glucofuranose;
1,2:5,6-di-O-isopropylidene-3-O-(3'-hexylbenzyl)-a-D-glucofuranose;
1,2:5,6-di-O-(1-methylpropylidene)-3-O-(3'-hexylbenzyl)-a-D-glucofuranose;
1,2:5,6-di-O-(1-ethylpropylidene)-3-O-(3'-hexylbenzyl)-a-D-glucofuranose; and
1,2:5,6-di-O-(1-propylbutylidene)-3-O-(3'-hexylbenzyl)-a-D-glucofuranose;
1,2:5,6-di-O-isopropylidene-3-O-(2'-bromobenzyl)-a-D-glucofuranose;
1,2:5,6-di-O-(1-methylpropylidene)-3-O-(2'-bromobenzyl)-a-D-glucofuranose;
1,2:5,6-di-O-(1-ethylpropylidene)-3-O-(2'-bromobenzyl)-a-D-glucofuranose; and
1,2:5,6-di-O-(1-propylbutylidene)-3-O-(2'-bromobenzyl)-a-D-glucofuranose;
1,2:5,6-di-O-isopropylidene-3-O-(4'-methoxybenzyl)-a-D-glucofuranose;
1,2:5,6-di-O-(1-methylpropylidene)-3-O-(4'-methoxybenzyl)-a-D-glucofuranose;
1,2:5,6-di-O-(1-ethylpropylidene)-3-O-(4'-methoxybenzyl)-a-D-glucofuranose;
1,2:5,6-di-O-(1-propylbutylidene)-3-O-(4'-methoxybenzyl)-a-D-glucofuranose;
1,2:5,6-di-O-(isopropylidene)-3-O-(2'-fluoro-4'-methylbenzyl)-a-D-glucofuranose;
1,2:5,6-di-O-(1-methylpropylidene)-3-O-(2'-fluoro-4'-methylbenzyl)-a-D-glucofuranose;
1,2:5,6-di-O-(1-ethylpropylidene)-3-O-(2'-fluoro-4'-methylbenzyl)-a-D-glucofuranose;
1,2:5,6-di-O-(1-propylbutylidene)-3-O-(2'-fluoro-4'-methylbenzyl)-a-D-glucofuranose;
1,2:5,6-di-O-isopropylidene-3-O-(2'3'4'5'tetramethylbenzyl)-a-D-glucofuranose;
1,2:5,6-di-O-(1-methylpropylidene)-3-O-(2'3'4'5'tetramethylbenzyl)-a-D-glucofuranose;
1,2:5,6-di-O-(1-ethylpropylidene)-3-O-(2'3'4'5'tetramethylbenzyl)-a-D-glucofuranose; and
1,2:5,6-di-O-(1-propylbutylidene)-3-O-(2'3'4'5'tetramethylbenzyl)-a-D-glucofuranose.

EXAMPLE 10

1,2-O-isopropylidene-3-O-(2'-chlorobenzyl)-a-D-glucofuranose

In this example 167.9 g of 1,2:5,6-di-O-isopropylidene-3-O-(2'-chlorobenzyl)-a-D-glucofuranose was stirred in a mixture of 495 ml of acetic acid and 275 ml of water at 40°–45° C. for about 12 hours. The reaction was monitored by thin layer chromatography. The reaction mixture was then cooled to room temperature and the acetic acid was then carefully neutralized by the slow addition of an aqueous saturated potassium carbonate solution and then extracted three times with 500 ml of methylene chloride. The extracts were combined and then washed twice with water and then with a saturated sodium chloride solution. The washed extracts were then dried over magnesium sulfate and evaporated under reduced pressure affording the title compound as a straw colored syrup.

Similarly, by following the same procedure, the 5,6-isopropylidene moieties are selectively hydrolyzed from the products of Example 9.

EXAMPLE 11

1,2-O-isopropylidene-3-O-(2'-chlorobenzyl)-5-deoxy-5-C-methylene-a-D-xylofuranose In this example 36 g (0.24 mol) of triethylorthoformate and 2 mls of glacial acid was added to 37.6 g (0.109 mol) of 1,2-O-isopropylidene-3-O-(2'-chlorobenzyl)-a-D-glucofuranose. The resulting mixture was refluxed for six hours. Excess triethylorthoformate was then removed by evaporation at 0.5 mm Hg. The resulting residue was then mixed three times with 100 mls of toluene followed by evaporation after each mixing to remove any traces of solvent affording 45.3 g of 1,2-O-isopropylidene-3-O-(2'-chlorobenzyl)-5,6-O-(ethoxymethylene)-a-D-glucofuranose as a yellow syrup.

45 g of this product was then mixed with 0.5 g triphenyl acetic acid and then heated at 170° C. (0.5 mm Hg) for 6 hours to distill off the ethanol byproduct of the reaction. The resulting syrup was then diluted with 300 ml of ethyl ether and then neutralized by the addition of sodium bicarbonate. The mixture was vigorously stirred and filtered. The resulting filtrate was washed twice with aqueous sodium bicarbonate, dried over magnesium sulfate and then evaporated. The resulting residue was distilled at 175°-178° C., 1.2 mm Hg yielding the title compound as a yellow syrup.

Similarly, by following the same procedure, using the corresponding products of Example 10 as starting materials, the following compounds are respectively prepared:

1,2-O-(1-methylpropylidene)-3-O-(2'-chlorobenzyl)-5-deoxy-5-C-methylene-a-D-xylofuranose;

1,2-O-(1-ethylpropylidene)-3-O-(2'-chlorobenzyl)-5-deoxy-5-C-methylene-a-D-xylofuranose; and 1,2-O-(1-propylbutylidene)-3-O-(2'-chlorobenzyl)-5-deoxy-5-C-methylene-a-D-xylofuranose.

EXAMPLE 12

1,2-O-isopropylidene-3-O-benzyl-5-deoxy-5-C-methylmethylene-a-D-xylofuranose (R is $CH_3CH=CH-$)

The title compound can be prepared by the following procedure: 3.7 g (0.01 mol) of triphenylethyl phosphonium bromide is added in portions to a solution of 0.01 mol of n-butyllithium in 100 ml of tetrahydrofuran with stirring under nitrogen. After stirring for 4 hours at room temperature, 2.8 g (0.01 mol) of 3-O-benzyl-1,2-O-isopropylidene-a-D-xylo-pentodialdo-1,4-furanose [Carbohydrate Research 14, 159-171 (1970)] dissolved in 20 ml of tetrahydrofuran is added dropwise and stirred overnight. The solvents are evaporated and the residue is treated with hexane-ethyl ether to precipitate solids. After filtration, the filtrate is concentrated under reduced pressure and purified by flash column chromatography employing tetrahydrofuran-hexane (1:4 by volume) as eluent to afford the title compound.

EXAMPLE 12a 1,2-O-isopropylidene-3-O-benzyl-5-deoxy-5-C-vinylmethyl-a-D-xylofuranose (R is $CH_2=CH-CH_2-$)

The title compound can be prepared by the following procedure: treatment of 3.6 g (0.01 mol) of triphenylmethyl phosphonium bromide with 2.9 g (0.01 mol) of 3-O-benzyl-5-deoxy-1,2-O-isopropylidene-a-D-xylohexodialdo-1,4-furanose [Helv. Chim. Acta 63, 1644 (1980)] in a similar manner as described in Example 12 will afford the title compound.

EXAMPLE 12b 1,2-O-isopropylidene-3-O-benzyl-5-deoxy-5-C-dimethyl-a-D-xylofuranose (R is isopropyl)

The title compound can be prepared by the following procedure: 3.6 g (0.01 mol) of triphenylmethylphosphonium bromide is reacted with 3.0 g (0.01 mol) of 3-O-benzyl-6-deoxy-1,2-O-isopropylidene-a-D-xylo-hexofuranos-5-ulose [Carbohydrate Research, 31, 387–396 (1973)] in the same manner as described in Example 12 and hydrogenated at 20 psi of hydrogen pressure employing 0.5 g of 5 wt. % palladium on charcoal catalyst as described in Example 15 to afford the title compound.

EXAMPLE 13

1,2-O-methylidene-3-O-benzyl-5-deoxy-5-C-methylene-a-D-xylofuranose

In this example, a mixture containing 5.5 g (0.02 mol) of 1,2-O-isopropylidene-3-O-benzyl-5-deoxy-5-C-methylene-a-D-xylofuranose, 10 g of paraformaldehyde in 35 mls of glacial acetic acid was heated at 70°-80° C. for 15 minutes. 2.75 g of concentrated sulfuric acid was then added and the mixture then heated at 70°-80° C. for an additional two hours. The mixture is cooled and then water added. The mixture was then extracted with methylene chloride. The combined extracts were washed with water, quenched with solid sodium bicarbonate and then washed with water until neutral. The neutralized mixture was dried over magnesium sulfate, evaporated, and then distilled at 150°-184° C. at 1 mm of Hg. The residue was then chromatographed on silica gel eluting with tetrahydrofurane-hexane mixtures (1:4 by volume). The entire procedure was repeated twice more affording 4.2 g of the title product as a colorless liquid.

Similarly, by following the same procedure using the 1,2-O-isopropylidene products of Examples 4, 7 and 11 as starting materials, the corresponding 1,2-O-methylidene homologs of these products are prepared.

Similarly, by following a similar procedure but using acetaldehyde in place of paraformaldehyde, the corresponding 1,2-O-ethylidene homologs of each of the 1,2-O-methylidene products are respectively prepared.

EXAMPLE 14

1,2-O-(1-ethylpropylidene)-3-O-benzyl-5-deoxy-5-C-methyl-a-D-xylofuranose

In this example a mixture containing 5.6 (0.02 mol) of 1,2-O-isopropylidene-3-O-benzyl-5-deoxy-5-C-methyl-a-D-xylofuranose in 40 mls of a mixture of trifluoroacetic acid and water containing 9 parts by volume of trifluoroacetic acid per part of water was stirred for one hour at room temperature. The solvents were then removed by rotary evaporation at 50°-55° C. The resulting residue was mixed with 30 mls of pentanone, 0.5 ml of concentrated sulfuric acid and 5 g of anhydrous copper sulfate. This mixture was stirred overnight (about 12-15 hours) at room temperature. Examination by thin layer chromatography showed completion of the reaction. Powdered anhydrous sodium carbonate was then added and stirred followed by the addition of 200 mls of ethyl ether and then saturated aqueous sodium bicarbonate. The ethyl ether layer was separated, washed with water until neutral and then dried over anhydrous magnesium sulfate and concentrated by vacuum evaporation. The concentrate was flash column chromatographed eluting with tetrahydrofuranhexane mixtures (1:6 by volume) affording 3.2 g of the title compound as a colorless liquid.

Similarly, by following the same procedure using the 1,2-O-isopropylidene or other 1,2-O-alkylidene products of Examples 4, 7 and 11 as starting materials the corresponding 1,2-O-(1-ethylpropylidene) homologs of each of those products are respectively prepared.

Similarly, by following the same procedure but using other aldehydes or ketones in place of pentanone, the corresponding 1,2-O-alkylidene or 1,2-O-(1-substituted-alkylidene) homologs are prepared.

EXAMPLE 15

1,2-O-isopropylidene-3-O-(2'-chlorobenzyl)-5-deoxy-5-C-methyl-α-D-xylofuranose

In this example 6 g of 1,2-O-isopropylidene-3-O-(2'-chlorobenzyl)-5-deoxy-5-C-methylene-a-D-xylofuranose were dissolved in 150 mls of ethanol and then 1.5 g of 5 wt. % palladium on charcoal catalyst is added. This mixture was then hydrogenated at 20 psig of hydrogen pressure for 20 minutes. The mixture was then filtered through diatomaceous earth, then evaporated affording a solid. This solid was then dissolved in 100 ml of methylene chloride, then washed with water and dried over magnesium sulfate and evaporated under vacuum. The residue was then recrystallized from a mixture of ethanol and water affording 3.6 g of the title compound as a white powder m.p. 68°-69° C.

Similarly, by following the same procedure, portions of the products of Examples 11, 12, and 13 are respectively hydrogenated to the corresponding saturated alkyl compound.

EXAMPLE 16

By applying the appropriate procedures described in the above examples and the appropriate starting materials, the compounds listed in Table A hereinbelow were prepared.

TABLE A

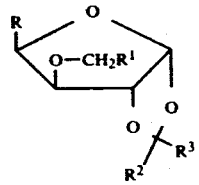

| No. | R | $R^1$ | $R^2$ | $R^3$ | Carbon Calc. | Carbon Found | Hydrogen Calc. | Hydrogen Found | Nitrogen Calc. | Nitrogen Found |
|---|---|---|---|---|---|---|---|---|---|---|
| 1 | —CH$_3$ | φ* | —CH$_3$ | —CH$_3$ | 68.16 | 68.14 | 7.63 | 7.90 | 0 | 0.09 |
| 2 | —CH$_2$CH$_3$ | φ | —CH$_3$ | —CH$_3$ | 69.04 | 67.90 | 7.97 | 7.90 | 0 | 0.34 |
| 3 | —CH$_2$CH$_3$ | 2-Cl—φ | —CH$_3$ | —CH$_3$ | 61.44 | 63.11 | 6.77 | 7.12 | 0 | 0.09 |
| 4 | —CH$_2$CH$_3$ | 2-F—φ | —CH$_3$ | —CH$_3$ | 64.85 | 63.75 | 7.14 | 7.27 | — | — |
| 5 | —CH$_2$CH$_3$ | 2-CH$_3$—φ | —CH$_3$ | —CH$_3$ | 69.84 | 71.33 | 8.27 | 9.06 | — | — |
| 6 | —CH$_2$CH$_3$ | 2-Cl—6-Cl—φ | —CH$_3$ | —CH$_3$ | 55.34 | 56.34 | 5.81 | 6.15 | 0 | 0.01 |
| 7 | —CH$_2$CH$_2$CH$_3$ | φ | —CH$_3$ | —CH$_3$ | 69.84 | 69.90 | 8.27 | 8.70 | 0 | 0.04 |
| 8 | —CH$_2$(CH$_2$)$_2$CH$_3$ | φ | —CH$_3$ | —CH$_3$ | 70.56 | 71.05 | 8.55 | 8.30 | 0 | 0.57 |
| 9 | —CH=CH$_2$ | φ | —CH$_3$ | —CH$_3$ | 69.54 | 68.90 | 7.29 | 7.71 | 0 | 0.22 |
| 10 | —CH=CH$_2$ | 2-Cl—φ | —CH$_3$ | —CH$_3$ | 61.84 | 64.19 | 6.16 | 6.48 | 0 | 0.08 |
| 11 | —CH=CH$_2$ | 2-F—φ | —CH$_3$ | —CH$_3$ | 65.29 | 68.58 | 6.51 | 7.11 | — | — |
| 12 | —CH=CH$_2$ | 2-CH$_3$—φ | —CH$_3$ | —CH$_3$ | 70.32 | 73.65 | 6.60 | 8.03 | — | |
| 13 | —CH=CH$_2$ | 2-Cl—6-Cl—φ | —CH$_3$ | —CH$_3$ | 55.67 | 56.36 | 5.26 | 5.52 | 0 | 0.06 |
| 14 | —CH$_2$CH$_3$ | φ | H | H | 67.18 | 67.65 | 7.25 | 7.60 | 0 | 0.02 |
| 15 | —CH$_2$CH$_3$ | φ | CH$_3$CH$_2$ | CH$_3$CH$_2$ | 70.56 | 71.60 | 8.55 | 8.98 | 0 | 0.42 |
| 16 | —CH=CH$_2$ | φ | H | H | 67.73 | 67.38 | 6.50 | 6.82 | 0 | 0.01 |
| 17 | —CH=CH$_2$ | φ | CH$_3$CH$_2$ | CH$_3$CH$_2$ | 71.03 | 70.96 | 7.95 | 7.84 | 0 | 0.03 |
| 18 | —CH=CH$_2$ | 4-F—φ | —CH$_3$ | —CH$_3$ | 65.29 | 65.45 | 6.51 | 6.67 | — | — |
| 19 | —CH$_2$CH$_3$ | 4-F—φ | —CH$_3$ | —CH$_3$ | 64.85 | 65.65 | 7.14 | 7.42 | — | — |
| 20 | —CH=CH$_2$ | 3-Cl—φ | —CH$_3$ | —CH$_3$ | 61.43 | 62.15 | 6.77 | 6.91 | — | — |
| 21 | —CH=CH$_2$ | 4-Cl—φ | —CH$_3$ | —CH$_3$ | 61.83 | 62.25 | 6.16 | 6.36 | — | — |
| 22 | —CH$_2$CH$_3$ | 4-Cl—φ | —CH$_3$ | —CH$_3$ | 61.43 | 62.51 | 6.77 | 7.09 | — | — |
| 23C** | —CH=CH$_2$ | 2,4-Cl$_2$—φ | —CH$_3$ | —CH$_3$ | 55.66 | 56.14 | 5.25 | 5.43 | — | — |
| 24 | —CH$_2$CH$_3$ | 2,4-Cl$_2$—φ | —CH$_3$ | —CH$_3$ | 55.34 | 56.09 | 5.81 | 6.10 | — | — |
| 25C | —CH=CH$_2$ | 3,4-Cl$_2$—φ | —CH$_3$ | —CH$_3$ | 55.66 | 56.57 | 5.25 | 6.22 | — | — |
| 26 | —CH$_2$CH$_3$ | 3,4-Cl$_2$—φ | —CH$_3$ | —CH$_3$ | 55.34 | 55.46 | 5.81 | 6.60 | — | — |
| 27 | —CH=CH$_2$ | 3-CH$_3$—φ | —CH$_3$ | —CH$_3$ | 70.32 | 69.62 | 7.64 | 8.72 | — | — |
| 28 | —CH$_2$CH$_3$ | 3-CH$_3$—φ | —CH$_3$ | —CH$_3$ | 69.84 | 69.04 | 8.27 | 8.38 | — | — |
| 29 | —CH=CH$_2$ | 4-CH$_3$—φ | —CH$_3$ | —CH$_3$ | 70.32 | 72.37 | 7.64 | 8.06 | — | — |
| 30 | —CH$_2$CH$_3$ | 4-CH$_3$—φ | —CH$_3$ | —CH$_3$ | 69.84 | 69.62 | 8.27 | 8.48 | 0 | 0.68 |
| 31C** | —CH=CH$_2$ | 3-CF$_3$—φ | —CH$_3$ | —CH$_3$ | 59.30 | 59.64 | 5.56 | 5.80 | — | — |
| 32C | —CH$_2$CH$_3$ | 3-CF$_3$—φ | —CH$_3$ | —CH$_3$ | 58.95 | 60.12 | 6.11 | 6.59 | 0 | 0.64 |
| 33 | —CH=CH$_2$ | 2-OCH$_3$—φ | —CH$_3$ | —CH$_3$ | 66.65 | 67.19 | 7.24 | 7.63 | — | — |
| 34 | —CH$_2$CH$_3$ | 2-OCH$_3$—φ | —CH$_3$ | —CH$_3$ | 66.21 | 66.25 | 7.84 | 8.15 | — | — |
| 35 | —CH=CH$_2$ | 4-OCH$_3$—φ | —CH$_3$ | —CH$_3$ | 66.65 | 67.53 | 7.24 | 7.84 | | |
| 36 | —CH$_2$CH$_3$ | 4-OCH$_3$—φ | —CH$_3$ | —CH$_3$ | 66.21 | 66.74 | 7.84 | 8.24 | — | — |
| 37 | —CH$_3$ | 2-Cl—φ | —CH$_3$ | —CH$_3$ | 60.30 | 60.36 | 6.41 | 6.61 | 0 | 0.05 |
| 38 | —CH$_2$CH$_2$CH$_3$ | 2-Cl—φ | —CH$_3$ | —CH$_3$ | 62.48 | 61.56 | 7.09 | 7.33 | 0 | 0.02 |
| 39 | —CH$_2$CH$_3$ | 1-naphthyl | —CH$_3$ | —CH$_3$ | 73.14 | 74.45 | 7.37 | 7.40 | — | — |

TABLE A-continued

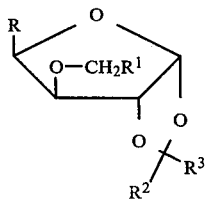

| No. | R | R¹ | R² | R³ | ELEMENTAL ANALYSIS | | | | | |
|---|---|---|---|---|---|---|---|---|---|---|
| | | | | | Carbon | | Hydrogen | | Nitrogen | |
| | | | | | Calc. | Found | Calc. | Found | Calc. | Found |
| 40 | —CH$_2$CH$_3$ | 3-Cl—φ | —CH$_3$ | —CH$_3$ | 61.43 | 62.15 | 6.77 | 6.91 | — | — |

*φ = phenyl
**Compounds with a "C" number are comparison compounds

A number of tetrahydrofuran compounds, including the C-3 epimers of Compounds 2 and 9 of the present invention, were prepared for the purposes of conducting comparison by logical activity stage.

TABLE B
Comparison Compounds

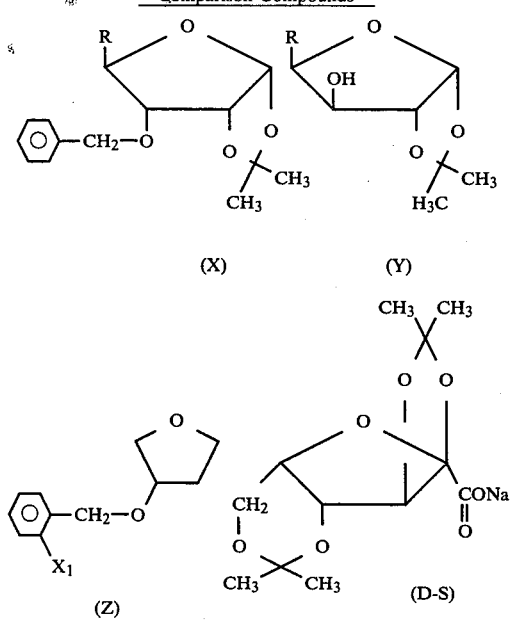

| Formula No. | R | X$_1$ | Elemental Analysis | | | | | |
|---|---|---|---|---|---|---|---|---|
| | | | Carbon | | Hydrogen | | Nitrogen | |
| | | | Calc. | Fd. | Calc. | Fd. | Calc. | Fd. |
| X-1 | —CH$_2$CH$_3$ | — | 69.04 | 70.68 | 7.97 | 8.02 | 0 | 0.01 |
| X-2 | —CH=CH$_2$ | — | 69.54 | 72.64 | 7.29 | 7.70 | 0 | 0.23 |
| Y-1 | —CH$_2$CH$_2$CH$_3$ | — | 59.39 | 59.79 | 8.97 | 9.32 | 0 | 0.01 |
| Y-2 | —(CH$_2$)$_3$CH$_3$ | — | 61.09 | 63.18 | 9.32 | 9.52 | 0 | 0.19 |
| Z-1 | — | H | 74.13 | 74.52 | 7.92 | 8.18 | 0 | 0 |
| Z-2 | — | Cl | 62.12 | 60.86 | 6.16 | 5.84 | 0 | 0.28 |
| D-S | — | — | — | — | — | — | — | — |

EXAMPLE 17

In this example, the compounds of Table A and the comparison compounds listed in Table B were repectively tested for pre-emergent and post-emergent activity against a variety of grasses and broad-leaf plants including one grain crop and one broad-leaf crop. The compounds tested are identified in Tables A and B hereinbelow.

Pre-Emergent Herbicide Test

Pre-emergence herbicidal activty was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface at a dose of 27.5 micrograms/cm$^2$. The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0- to 100-scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm$^2$. After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0- to 100-scale was used, 0 representing no phytotoxicity, 100 representing complete kill. The results of these tests are summarized in Table 2.

TABLE 1

Pre-Emergence Herbicidal Activity

| Compound No. | Broad-Leaf Plants % Phytotoxicity | | | | Grasses % Phytotoxicity | | | |
|---|---|---|---|---|---|---|---|---|
| | Lambs Quarter | Mustard | Pigweed | Soybean | Crab Grass | Water Grass | Wild Oats | Rice |
| 1 | 0 | 0 | 15 | 0 | 98 | 100 | 80 | 100 |
| 2 | 65 | 25 | 68 | 50 | 100 | 100 | 96 | 100 |
| 3 | 65 | 58 | 45 | 60 | 100 | 100 | 85 | 98 |
| 4 | 65 | 15 | 60 | 35 | 100 | 100 | 99 | 99 |
| 5 | 83 | 38 | 45 | 55 | 100 | 100 | 75 | 100 |
| 6 | 65 | 50 | 45 | 28 | 100 | 100 | 45 | 58 |
| 7 | 0 | 0 | 0 | 0 | 100 | 100 | 93 | 100 |
| 8 | 20 | 0 | 0 | 10 | 93 | 100 | 25 | 0 |
| 9 | 55 | 25 | 60 | 0 | 100 | 100 | 70 | 88 |
| 10 | 55 | 18 | 0 | 0 | 99 | 99 | 35 | 40 |
| 11 | 60 | 13 | 40 | 35 | 100 | 100 | 15 | 60 |
| 12 | 67 | 0 | 25 | 0 | 100 | 99 | 0 | 23 |
| 13 | 55 | 35 | 15 | 23 | 75 | 80 | 20 | 25 |
| 14 | 25 | 0 | 15 | 35 | 100 | 100 | 0 | 90 |
| 15 | 10 | 0 | 30 | 10 | 100 | 100 | 0 | 93 |
| 16 | 0 | 0 | 0 | 0 | 95 | 100 | 0 | 20 |
| 17 | 10 | 0 | 10 | 0 | 100 | 100 | 0 | 25 |
| 18 | 40 | 15 | 45 | 0 | 80 | 80 | 0 | 58 |
| 19 | 60 | 60 | 60 | 25 | 100 | 100 | 90 | 99 |
| 20* | — | — | — | — | — | — | — | — |
| 21 | 0 | 0 | 43 | 35 | 88 | 58 | 0 | 0 |
| 22 | 65 | 20 | 60 | 0 | 100 | 100 | 63 | 60 |
| 23 | 0 | 0 | 0 | 0 | 0 | 0 | 0 | 0 |
| 24 | 0 | 0 | 0 | 0 | 92 | 75 | 0 | 0 |
| 25 | 0 | 0 | 0 | 0 | 0 | 0 | 0 | 0 |
| 26 | 0 | 0 | 0 | 0 | 20 | 55 | 0 | 0 |
| 27 | 0 | 0 | 0 | 0 | 55 | 65 | 0 | 0 |
| 28 | 60 | 15 | 0 | 0 | 99 | 100 | 35 | 60 |
| 29 | 0 | 0 | 0 | 0 | 60 | 75 | 0 | 0 |
| 30 | 50 | 30 | 55 | 35 | 100 | 100 | 30 | 70 |
| 31 | 0 | 0 | 0 | 0 | 0 | 0 | 0 | 0 |
| 32 | 0 | 0 | 0 | 0 | 0 | 0 | 0 | 0 |
| 33 | 63 | 35 | 65 | 0 | 15 | 100 | 63 | 15 |
| 34 | 70 | 18 | 65 | 0 | 75 | 30 | 65 | 40 |
| 35 | 50 | 30 | 60 | 0 | 50 | 0 | 65 | 0 |
| 36 | 50 | 40 | 53 | 10 | 94 | 43 | 63 | 50 |
| 37 | 0 | 0 | 40 | 0 | 100 | 100 | 55 | 60 |
| 38 | 65 | 0 | 0 | 0 | 100 | 100 | 65 | 63 |
| 39 | 52 | 0 | 0 | 20 | 80 | 80 | 0 | 0 |
| 40 | 55 | 0 | 30 | 20 | 99 | 100 | 35 | 30 |
| X-1 | 0 | 0 | 0 | 0 | 0 | 0 | 0 | 0 |
| X-2 | 0 | 0 | 0 | 0 | 0 | 0 | 0 | 0 |
| Y-1 | 0 | 0 | 0 | 0 | 0 | 0 | 0 | 0 |
| Y-2 | 0 | 0 | 0 | 0 | 0 | 0 | 0 | 0 |
| Z-1 | 10 | 0 | 15 | 10 | 98 | 99 | 60 | 100 |
| Z-2 | 10 | 10 | 10 | 0 | 100 | 98 | 60 | 97 |
| D-S | 0 | 83 | 55 | 45 | 43 | 40 | 0 | 65 |

*Not tested

TABLE 2

Post-Emergence Herbicidal Activity

| Compound No. | Broad-Leaf Plants % Phytotoxicity | | | | Grasses % Phytotoxicity | | | |
|---|---|---|---|---|---|---|---|---|
| | Lambs Quarter | Mustard | Pigweed | Soybean | Crab Grass | Water Grass | Wild Oats | Rice |
| 1 | 0 | 0 | 0 | 0 | 0 | 0 | 0 | 0 |
| 2 | 0 | 0 | 0 | 0 | 45 | 80 | 60 | 10 |
| 3 | 70 | 65 | 60 | 68 | 40 | 65 | 0 | 0 |
| 4 | 50 | 15 | 0 | 55 | 50 | 80 | 60 | 35 |
| 5 | 55 | 40 | 25 | 60 | 20 | 45 | 0 | 0 |
| 6 | 60 | 45 | 38 | 60 | 30 | 65 | 0 | 0 |
| 7 | 0 | 0 | 0 | 0 | 0 | 0 | 0 | 0 |
| 8 | 0 | 0 | 0 | 0 | 0 | 0 | 0 | 0 |
| 9 | 0 | 0 | 0 | 0 | 0 | 0 | 0 | 0 |
| 10 | 15 | 0 | 0 | 55 | 0 | 0 | 0 | 0 |
| 11 | 15 | 0 | 0 | 15 | 0 | 0 | 0 | 0 |
| 12 | 20 | 0 | 0 | 45 | 0 | 0 | 0 | 0 |
| 13 | 35 | 0 | 0 | 10 | 0 | 0 | 0 | 0 |
| 14 | 0 | 0 | 0 | 0 | 0 | 0 | 0 | 0 |
| 15 | 0 | 0 | 0 | 0 | 0 | 0 | 0 | 0 |
| 16 | 0 | 0 | 0 | 0 | 0 | 0 | 0 | 0 |
| 17 | 0 | 0 | 0 | 0 | 0 | 0 | 0 | 0 |
| 18 | 0 | 0 | 0 | 18 | 0 | 0 | 0 | 0 |
| 19 | 0 | 0 | 0 | 0 | 22 | 75 | 50 | 0 |
| 20* | — | — | — | — | — | — | — | — |
| 21 | 0 | 0 | 0 | 0 | 0 | 0 | 0 | 0 |
| 22 | 0 | 0 | 0 | 0 | 0 | 0 | 0 | 0 |
| 23 | 0 | 0 | 0 | 0 | 0 | 0 | 0 | 0 |
| 24 | 0 | 20 | 0 | 0 | 0 | 0 | 0 | 0 |
| 25 | 0 | 0 | 0 | 0 | 0 | 0 | 0 | 0 |
| 26 | 0 | 0 | 0 | 0 | 0 | 0 | 0 | 0 |
| 27 | 0 | 0 | 0 | 0 | 0 | 0 | 0 | 0 |
| 28 | 0 | 0 | 0 | 23 | 0 | 0 | 0 | 0 |
| 29 | 0 | 0 | 0 | 20 | 0 | 0 | 0 | 0 |
| 30 | 0 | 0 | 0 | 45 | 0 | 45 | 0 | 0 |
| 31 | 0 | 0 | 0 | 0 | 0 | 0 | 0 | 0 |
| 32 | 0 | 0 | 0 | 0 | 0 | 0 | 0 | 0 |
| 33 | 0 | 0 | 0 | 25 | 0 | 0 | 0 | 0 |
| 34 | 0 | 15 | 35 | 0 | 0 | 0 | 0 | 0 |
| 35 | 0 | 0 | 0 | 0 | 0 | 0 | 0 | 0 |
| 36 | 0 | 0 | 0 | 0 | 0 | 0 | 0 | 0 |
| 37 | 0 | 0 | 0 | 0 | 0 | 0 | 0 | 0 |
| 38 | 60 | 15 | 20 | 63 | 0 | 0 | 0 | 0 |
| 39 | 40 | 0 | 0 | 0 | 0 | 0 | 0 | 0 |
| 40 | 0 | 0 | 0 | 18 | 0 | 0 | 0 | 0 |
| X-1 | 0 | 0 | 0 | 0 | 0 | 0 | 0 | 0 |
| X-2 | 0 | 0 | 0 | 0 | 0 | 0 | 0 | 0 |
| Y-1 | 0 | 0 | 0 | 0 | 0 | 0 | 0 | 0 |
| Y-2 | 0 | 0 | 0 | 0 | 0 | 0 | 0 | 0 |
| Z-1 | 0 | 0 | 0 | 0 | 0 | 0 | 0 | 0 |
| Z-2 | 0 | 0 | 0 | 0 | 0 | 0 | 0 | 0 |
| D-S | 55 | 70 | 45 | 50 | 55 | 60 | 10 | 55 |

*Not tested

As can be seen from Tables 1 and 2, at the dosage tested the compositions of the present invention exhibited very good pre-emergence herbicide activity against grasses and in some instances also exhibited pre-emergence herbicide activity against broad-leaf plants and some post emergence activity. Comparison Compounds X-1 and X-2 (C-3 epimers of Compounds Nos. 2 and 9 respectively) were inactive as was the Compound Y-1 (the 3-hydroxy analog of Compound 7) and Y-2. Compound D.S. exhibited poor pre-emergence activity against grasses. Comparison Compounds Z-1 and Z-2 also exhibited pre-emergence activity against grasses.

EXAMPLE 18

In this example pre-emergence activity at reduced dosages was determined for certain of the compounds of Table A and Comparison Compounds Z-1 and Z-2. This test was conducted in the same manner as the test described in Example 17, hereinabove, except that the test formulations were further diluted to give the dosages indicated in Table 3 hereinbelow. The results of this test are summarized in Table 3 hereinbelow.

TABLE 3

Pre-Emergence Herbicidal Activity
Low Dosage Tests

| Compound No. | Dosage $\gamma/cm^2$* | Broad-Leaf Plants % Phytotoxicity | | | | Grasses % Phytotoxicity | | | |
|---|---|---|---|---|---|---|---|---|---|
| | | Lambs Quarter | Mustard | Pigweed | Soybean | Crab Grass | Water Grass | Wild Oats | Rice |
| 2 | 11 | 57 | 10 | 20 | 3 | 99 | 100 | 98 | 100 |
| 2 | 4.4 | 33 | 7 | 0 | 0 | 96 | 100 | 93 | 97 |
| 2 | 1.8 | 27 | 0 | 0 | 0 | 67 | 99 | 65 | 98 |
| 2 | 0.7 | 0 | 0 | 0 | 0 | 20 | 87 | 10 | 43 |
| 9 | 11 | 43 | 0 | 0 | 2 | 77 | 100 | 53 | 33 |
| 9 | 4.4 | 25 | 0 | 0 | 0 | 10 | 75 | 13 | 7 |
| 9 | 1.8 | 13 | 0 | 0 | 0 | 0 | 10 | 0 | 0 |
| 9 | 0.7 | 0 | 0 | 0 | 0 | 0 | 0 | 0 | 0 |
| Z-1 | — | — | — | — | — | — | — | — | — |
| Z-1 | 4.4 | 0 | 0 | 0 | 0 | 0 | 20 | 47 | 0 |
| Z-1 | 1.8 | 0 | 0 | 0 | 0 | 0 | 0 | 10 | 0 |
| Z-1 | 0.7 | 0 | 0 | 0 | 0 | 0 | 0 | 0 | 0 |
| 3 | 11 | 52 | 27 | 23 | 10 | 100 | 100 | 77 | 98 |
| 3 | 4.4 | 42 | 0 | 0 | 8 | 96 | 99 | 55 | 75 |
| 3 | 1.8 | 20 | 0 | 0 | 3 | 82 | 99 | 20 | 33 |
| 3 | 0.7 | 20 | 0 | 0 | 0 | 57 | 99 | 0 | 10 |
| 10 | 11 | 43 | 0 | 0 | 7 | 62 | 99 | 0 | 0 |
| 10 | 4.4 | 33 | 0 | 0 | 0 | 7 | 75 | 0 | 0 |
| 10 | 1.8 | 0 | 0 | 0 | 0 | 0 | 60 | 0 | 0 |
| 10 | 0.7 | 0 | 0 | 0 | 0 | 0 | 40 | 0 | 0 |
| Z-2 | 11 | — | — | — | — | — | — | — | — |
| Z-2 | 4.4 | 0 | 0 | 0 | 0 | 0 | 53 | 0 | 0 |
| Z-2 | 1.8 | 0 | 0 | 0 | 0 | 0 | 0 | 0 | 0 |
| Z-2 | .7 | 0 | 0 | 0 | 0 | 0 | 0 | 0 | 0 |
| 4 | 11 | 63 | 0 | 60 | 2 | 100 | 100 | 95 | 100 |
| 4 | 4.4 | 58 | 0 | 43 | 0 | 98 | 100 | 80 | 100 |
| 4 | 1.8 | 45 | 0 | 20 | 0 | 73 | 98 | 30 | 62 |
| 4 | 0.7 | 5 | 0 | 18 | 0 | 33 | 73 | 3 | 8 |
| 5 | 11 | 57 | 3 | 27 | 0 | 97 | 100 | 42 | 100 |
| 5 | 4.4 | 50 | 0 | 23 | 0 | 87 | 98 | 23 | 77 |
| 5 | 1.8 | 40 | 0 | 13 | 0 | 62 | 87 | 3 | 22 |
| 5 | 0.7 | 35 | 0 | 3 | 0 | 7 | 68 | 0 | 0 |
| 1 | 11 | 43 | 0 | 50 | 0 | 47 | 82 | 0 | 52 |
| 1 | 4.4 | 33 | 0 | 22 | 0 | 0 | 47 | 0 | 23 |
| 1 | 1.8 | 0 | 0 | 0 | 0 | 0 | 0 | 0 | 0 |
| 1 | 0.7 | 0 | 0 | 0 | 0 | 0 | 0 | 0 | 0 |
| 8 | 11 | 0 | 0 | 0 | 0 | 0 | 0 | 0 | 0 |
| 8 | 4.4 | 0 | 0 | 0 | 0 | 0 | 0 | 0 | 0 |
| 8 | 1.8 | 0 | 0 | 0 | 0 | 0 | 0 | 0 | 0 |
| 8 | 0.7 | 0 | 0 | 0 | 0 | 0 | 0 | 0 | 0 |

*$\gamma/cm^2$ = micrograms per square centimeter

As can be seen from the results shown in Table 3, the compounds of Table A which were tested at low dosages generally exhibited excellent pre-emergence activity and greatly superior to the activity exhibited by Comparison Compounds Z-1 and Z-2.

EXAMPLE 19

In this example pre-emergence activity at reduced dosages were determined against an expanded variety of weeds for compound 2 of Table A, hereinabove, of the present invention and 3-O-benzyl-6,7-dideoxy-1,2-O-isopropylidene-a-D-xylo-heptofuranos-5-ulose (Formula X-3, wherein R is

$$-\overset{\overset{\text{O}}{\|}}{C}CH_2CH_3)$$

which is described as a herbicide in commonly assigned application Ser. No. 387,590, filed June 11, 1982, of B. McCaskey.

This test was conducted in the same manner as the test described in Example 17, hereinabove, with the exception of the increased dilution of the test compound and the expanded number of plant species. The results of this test are summarized in Tables 4–6 hereinbelow.

TABLE 4

Pre-Emergence Herbicidal Activity
Low Dosage Tests

| Compound No. | Dosage $\gamma/cm^2$* | Grasses % Phytotoxicity | | | | | | | | |
|---|---|---|---|---|---|---|---|---|---|---|
| | | Crab Grass | Water Grass | Wild Oats | Cheat Grass | Johnson Grass | Rye Grass | Switch Grass | Yellow Foxtail | Yellow Nutsedge |
| 2 | 11 | 99 | 100 | 98 | — | — | — | — | — | — |
| 2 | 4.4 | 96 | 100 | 93 | 100 | 72 | 100 | 99 | 100 | 62 |
| 2 | 1.8 | 67 | 99 | 65 | 95 | 48 | 91 | 93 | 90 | 33 |
| 2 | 0.7 | 20 | 87 | 10 | 47 | 15 | 55 | 37 | 67 | 0 |
| X-3 | 11 | 100 | 100 | 97 | — | — | — | — | — | — |
| X-3 | 4.4 | 100 | 100 | 88 | 100 | 72 | 100 | 100 | 100 | 95 |
| X-3 | 1.8 | 88 | 99 | 85 | 63 | 7 | 93 | 99 | 97 | 53 |

TABLE 4-continued

Pre-Emergence Herbicidal Activity
Low Dosage Tests

| Compound No. | Dosage $\gamma/cm^2$* | Grasses % Phytotoxicity | | | | | | | | |
|---|---|---|---|---|---|---|---|---|---|---|
| | | Crab Grass | Water Grass | Wild Oats | Cheat Grass | Johnson Grass | Rye Grass | Switch Grass | Yellow Foxtail | Yellow Nutsedge |
| X-3 | 0.7 | 70 | 98 | 53 | 38 | 0 | 65 | 43 | 70 | 27 |

*$\gamma/cm^2$ = micrograms per square centimeter

TABLE 5

Pre-Emergence Herbicidal Activity
Low Dosage Tests

| Compound No. | Dosage $\gamma/cm^2$* | Broad-Leaf Crops % Phytotoxicity | | | | | | |
|---|---|---|---|---|---|---|---|---|
| | | Soybean | Alfalfa | Cotton | Peanuts | Peas | Sugar Beets | Tomatoes |
| 2 | 11 | 3 | — | — | — | — | — | — |
| 2 | 4.4 | 0 | 2 | 0 | 0 | 83 | 57 | 53 |
| 2 | 1.8 | 0 | 3 | 0 | 0 | 60 | 32 | 35 |
| 2 | 0.7 | 0 | 0 | 0 | 0 | 28 | 15 | 3 |
| X-3 | 11 | 43 | — | — | — | — | — | — |
| X-3 | 4.4 | 7 | 23 | 23 | 15 | 72 | 75 | 75 |
| X-3 | 1.8 | 0 | 5 | 2 | 0 | 48 | 35 | 48 |
| X-3 | 0.7 | 0 | 0 | 0 | 0 | 32 | 20 | 37 |

*$\gamma/cm^2$ = micrograms per square centimeter

TABLE 6

Pre-Emergence Herbicidal Activity
Low Dosage Tests

| Compound No. | Dosage $\gamma/cm^2$* | Broad-Leaf Weeds % Phytotoxicity | | | Grass Crops % Phytotoxicity | | | | |
|---|---|---|---|---|---|---|---|---|---|
| | | Lambs Quarter | Mustard | Pigweed | Rice | Corn | Oats | Sorghum | Wheat Rice |
| 2 | 11 | 57 | 10 | 20 | 100 | — | — | — | — |
| 2 | 4.4 | 33 | 7 | 0 | 97 | 89 | 99 | 100 | 98 |
| 2 | 1.8 | 27 | 0 | 0 | 98 | 67 | 90 | 53 | 97 |
| 2 | 0.7 | 0 | 0 | 0 | 43 | 43 | 73 | 10 | 17 |
| X-3 | 11 | 62 | 47 | 33 | 100 | — | — | — | — |
| X-3 | 4.4 | 50 | 12 | 23 | 90 | 97 | 99 | 100 | 100 |
| X-3 | 1.8 | 37 | 3 | 0 | 63 | 70 | 85 | 70 | 92 |
| X-3 | 0.7 | 27 | 0 | 0 | 13 | 35 | 72 | 33 | 63 |

*$\gamma/cm^2$ = micrograms per square centimeter

As can be seen from Tables 4–6, both compounds exhibit exceptional pre-emergence grass herbicidal activity at reduced dosages and in addition, compound 2 exhibits excellent safety for use with soybean, alfalfa, cotton and peanut crops.

Obviously, many modifications and variations of the invention described hereinabove and below in the claims can be made without departing from the essence and scope thereof.

What is claimed is:

1. A compound having the formula:

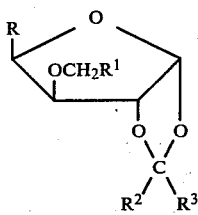

(I)

wherein

R is lower alkyl having 1 through 4 carbon atoms or alkenyl having 2 through 4 carbon atoms;

$R^1$ is 2-trifluoromethylphenyl, aryl having 6 through 10 carbon atoms or substituted aryl having 1 through 4 substituents independently selected from the group of lower alkyl having 1 through 4 carbon atoms, lower alkoxy having 1 through 4 carbon atoms, and halo, with the proviso that when $R^1$ is substituted aryl having more than two halo substituents or is 2,3- or 2,4-dihalophenyl, then R is alkyl; and $R^2$ and $R^3$ are independently hydrogen or lower alkyl with the proviso that when R is methyl, butyl, vinyl, 2-allyl or but-1-enyl, and $R^2$ and $R^3$ are each methyl, then $R^1$ is not phenyl.

2. The compound of claim 1 wherein $R^1$ is aryl or monosubstituted aryl having a sole substituent selected from the group of lower alkyl, lower alkoxy, and halo.

3. The compound of claim 2 wherein $R^1$ is phenyl or monosubstituted phenyl having its sole substituent at the 2 position.

4. The compound of claim 3 wherein R is lower alkyl.

5. The compound of claim 4 wherein R is ethyl or propyl and $R^1$ is phenyl, 2-chlorophenyl, or 2-fluorophenyl or 2-methylphenyl.

6. The compound of claim 5 wherein $R^2$ and $R^3$ are each methyl.

7. The compound of claim 1 wherein R is lower alkyl.

8. The compound of claim 7 wherein R is ethyl or propyl.

9. The compound of claim 1 wherein R is alkenyl having 2 through 4 carbon atoms.

10. The compound of claim 9 wherein $R^2$ and $R^3$ are each methyl and $R^1$ is phenyl, 2-chlorophenyl, 2-fluorophenyl or 2-methylphenyl.

11. The compound of claim 1 wherein $R^2$ and $R^3$ are each methyl.

12. The compound of claim 11 wherein R is ethyl and $R^1$ is phenyl.

13. The compound of claim 11 wherein R is ethyl and $R^1$ is 2-chlorophenyl.

14. The compound of claim 11 wherein R is ethyl and $R^1$ is 2-fluorophenyl.

15. The compound of claim 11 wherein R is ethyl and $R^1$ is 2-methylphenyl.

* * * * *